United States Patent [19]
Gilli

[11] Patent Number: 5,209,229
[45] Date of Patent: May 11, 1993

[54] APPARATUS AND METHOD EMPLOYING PLURAL ELECTRODE CONFIGURATIONS FOR CARDIOVERSION OF ATRIAL FIBRILLATION IN AN ARRHYTHMIA CONTROL SYSTEM

[75] Inventor: Norma L. Gilli, Elanora Heights, Australia

[73] Assignee: Telectronics Pacing Systems, Inc., Englewood, Colo.

[21] Appl. No.: 702,891

[22] Filed: May 20, 1991

[51] Int. Cl.$^5$ .............................................. A61N 1/39
[52] U.S. Cl. ............................................... 128/419 D
[58] Field of Search ................................... 128/419 D

[56] References Cited

U.S. PATENT DOCUMENTS

| | | | |
|---|---|---|---|
| 3,857,398 | 12/1974 | Rubin | 128/419 D |
| 3,937,226 | 2/1976 | Funke | 128/419 D |
| 4,572,191 | 2/1987 | Mirowski et al. | 128/419 D |
| 4,825,871 | 5/1989 | Cansell | 127/419 D |
| 4,869,252 | 9/1989 | Gilli | 128/419 PG |
| 4,895,151 | 1/1990 | Grevis et al. | 128/419 PG |
| 4,922,927 | 5/1990 | Fine et al. | 128/786 |
| 4,940,054 | 7/1990 | Grevis et al. | 128/419 PG |
| 4,998,974 | 3/1991 | Aker | 128/419 PG |
| 5,005,587 | 4/1991 | Scott | 128/786 |
| 5,063,928 | 11/1991 | Grevis et al. | 128/419 D |

FOREIGN PATENT DOCUMENTS 1076286  2/1960  Fed. Rep. of Germany ... 128/419 D

OTHER PUBLICATIONS

Langenfeld, H. et al., "Atrial Fibrillation and Embolic Complications", *PACE*, vol. 11, Nov. 1988, Part II, pp. 1667–1672.

Saksena, S. et al., "Comparative Efficacy of Transvenous Cardioversion and Pacing in Patients with Sustained Ventricualr Tachycardia: A Prospective Randomized, Crossover Study", *CIRCULATION*, vol. 72, No. 1, Jul. 1988, pp. 153–160.

Saksena, S. et al., "Transvenous Cardioversion and Defibrillation of Ventricular Tachyarrhythmias: Current Status and Future Direction", *PACE*, vol. 89, pp. 715–731 (Sep.–Oct. 1985).

Scott S. et al., "Defibrillation of Ventricular and Atrial Fibrillation Using New Transvenous Tripolar Leads With 5FR Shocking Electrodes and 8FR Subcutaneous Catheters," *PACE*, vol. 14, Apr. 1991, Part II, p. 676.

Primary Examiner—William E. Kamm
Attorney, Agent, or Firm—Gottlieb, Rackman & Reisman

[57] ABSTRACT

An implantable device and a method for the automatic detection of atrial arrhythmias and for providing low energy atrial cardioversion therapy for such arrhythmias, with minimal tissue damage and power drain, is disclosed. The device is capable of being incorporated within, and is disclosed as part of, an implantable automatic pacemaker defibrillator/cardioverter having the ability to also provide high energy ventricular defibrillation therapy, as well as dual chamber antitachycardia pacing therapy and bradycardia support pacing. Tripolar atrial and ventricular endocardial leads, each including tip and ring pacing electrodes and a braid cardioverting electrode therein, are employed in conjunction with a subcutaneous electrode lead in delivering therapy from the device to the patient, allowing the device to be implanted in and used by a patient without the need to open the patient's chest cavity. A number of different cardioverting electrode configurations are selectable for the multiple implantable electrodes, and automatic switching from one electrode configuration to another is employed if cardioversion is not achieved using the first configuration.

59 Claims, 12 Drawing Sheets

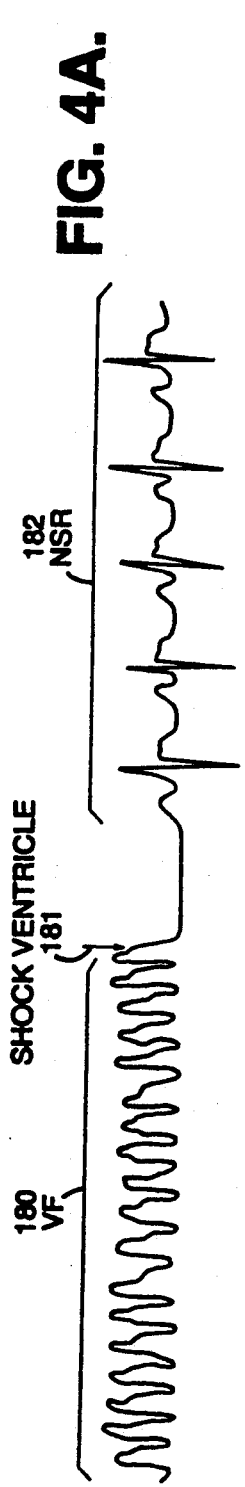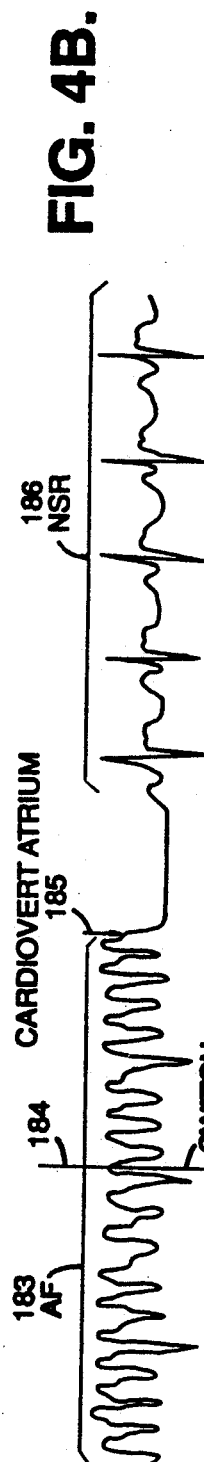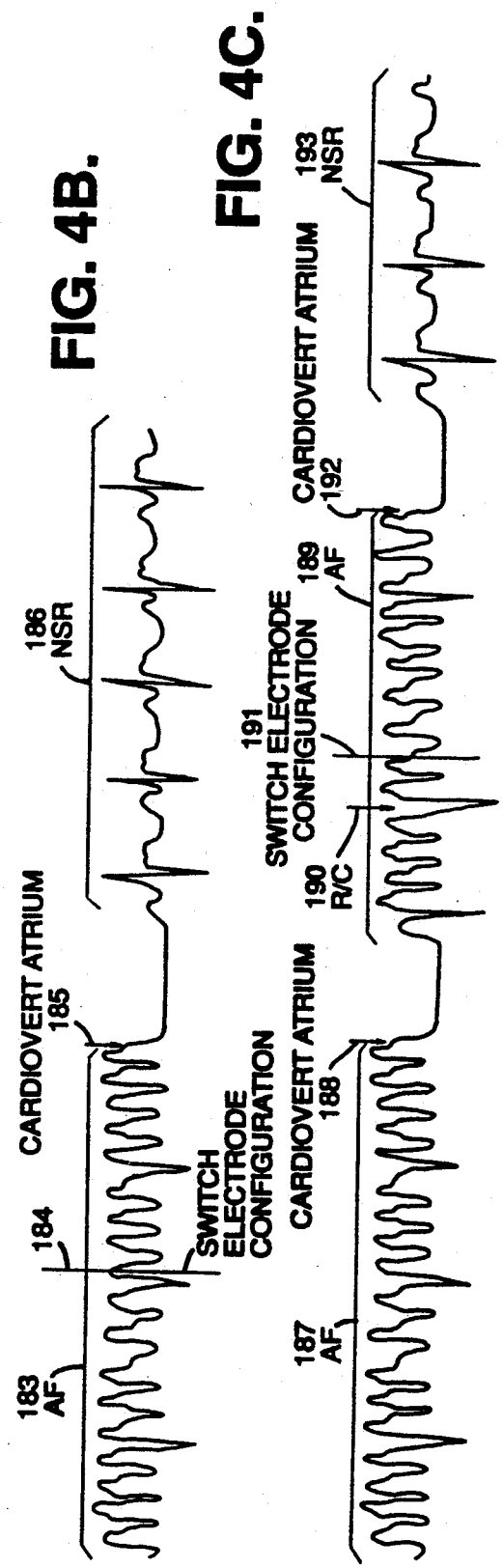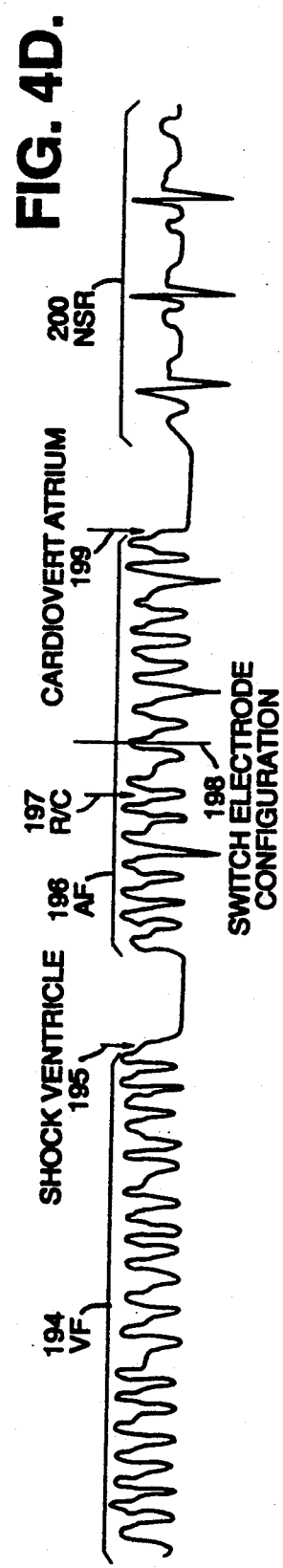

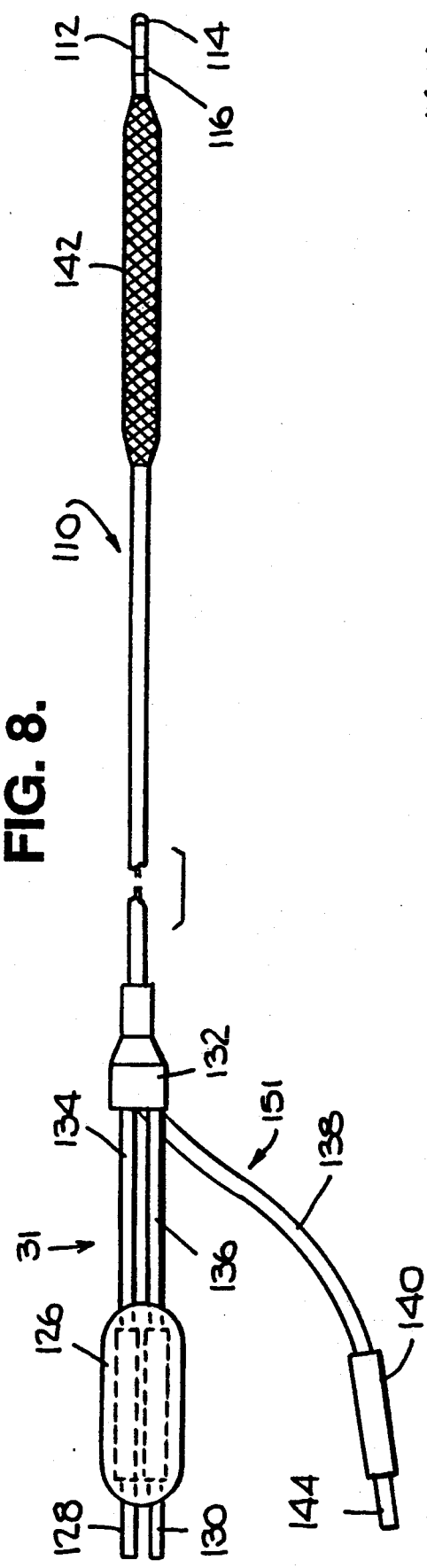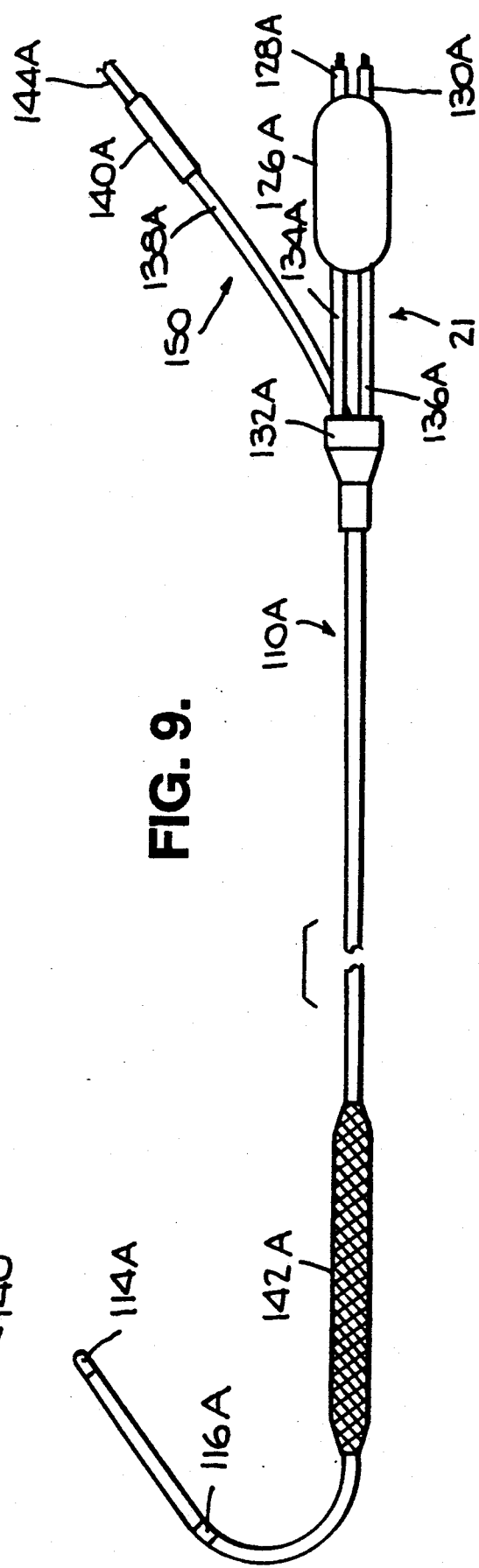
FIG. 8.
FIG. 9.

APPARATUS AND METHOD EMPLOYING PLURAL ELECTRODE CONFIGURATIONS FOR CARDIOVERSION OF ATRIAL FIBRILLATION IN AN ARRHYTHMIA CONTROL SYSTEM

TECHNICAL FIELD

This invention relates to implantable medical devices which monitor the cardiac state of a patient by sensing the patient's intrinsic rhythm, atrial and ventricular tachycardia and atrial and ventricular fibrillation/flutter, and which deliver therapy in the form of electrical energy to cardiac tissue in an attempt to revert tachycardia and restore a normal sinus rhythm. More particularly, the invention relates to an apparatus and method for cardioversion of atrial fibrillation/flutter in a dual chamber arrhythmia control system. Although the invention may be incorporated in a cardioversion device alone, it is described herein as operating in a combined implantable antitachycardia pacing, bradycardia pacing, defibrillating/cardioverting arrhythmia control system.

As used herein, the term ventricular tachycardia refers to any fast abnormal rhythm of the ventricle which may be amenable to treatment by electrical discharges and specifically includes ventricular tachycardia (VT), ventricular flutter and ventricular fibrillation (VF), while atrial tachycardia refers to atrial fibrillation (AF) and atrial flutter.

The term cardioversion refers to the discharge of electrical energy into the cardiac tissue in an attempt to terminate or revert a tachycardia and may range from a high (40 Joules or more) to a low (less than 1 Joule) energy discharge. Cardioversion usually refers to a low energy discharge such as the discharge delivered to the atrium according to the present invention. Defibrillation, however, usually refers to higher energy shocks such as are delivered to the ventricles. By definition, as used herein both in the description of the invention and in the claims, the two terms may be considered as interchangeable.

BACKGROUND OF THE INVENTION

Atrial fibrillations have been observed after termination of ventricular arrhythmias by cardioversion, as described in an article entitled "Comparative Efficacy of Transvenous Cardioversion and Pacing in Patients with Sustained Ventricular Tachycardia: A Prospective, Randomized, Crossover Study," by Saksena et al., in Circulation 72, No. 1, pages 153-160, 1985. Termination with transvenous cardioversion was followed by occurrences of atrial fibrillation, atrial flutter and sinus tachycardia. See, also, an article entitled "Transvenous Cardioversion and Defibrillation of Ventricular Tachyarrhythmias: Current Status and Future Directions," by Saksena et al., in PACE, Vol 8, pages 715-731, 1985. In this study, the incidence of supraventricular tachyarrhythmias after transvenous cardioversion was substantial. Such problems continue to exist.

In patients receiving cardioversion shocks using prior art devices, it has been observed in some cases that such post-therapy arrhythmias have been attributable to the shock being delivered during the vulnerable zone of the atrium. In those cases where atrial arrhythmias occur at a sufficiently fast rate, there is a likelihood of this arrhythmia being detected as VT/VF, resulting in the patient receiving an unnecessary shock to the ventricles of the patient's heart. This highlights the need for an implantable device having the capability of effectively sensing atrial fibrillation, and having the ability both to switch to an atrial cardioversion configuration and to synchronize atrial cardioversion shocks to the ventricular rhythm of the patient, thereby to successfully treat atrial arrhythmias such as atrial fibrillation and atrial flutter.

An article entitled "Atrial Fibrillation and Embolic Complications in Paced Patients," by H. Langenfeld et al., in PACE, Vol. 11, pages 1667-1672, 1985, shows the high incidence of atrial fibrillation in patients with VVI pacemakers. This is said to be attributable to irritation of the atrial rhythm caused by retrograde conduction. Thus, certain combined implantable defibrillator/pacemakers not only may contribute to the cause of the problem of atrial fibrillation, but also have been found to lack the facilities to deal successfully with atrial arrhythmias. Thus, there is a need for implantable devices capable of successfully treating atrial arrhythmias.

U.S. Pat. No. 3,857,398 to Rubin describes a combined pacer/defibrillator. This device performs either a pacing or a defibrillation function, depending on the detection of a VT/VF. If a VT/VF is detected, the device is switched to the defibrillating mode. After a period of time to charge the capacitor, a defibrillation shock is delivered to the patient.

A multiprogrammable, telemetric, implantable defibrillator is disclosed in the co-pending U.S. patent application Ser. No. 576,178 of Norma L. Gilli et al., entitled "Reconfirmation Prior to Shock for Implantable Defibrillation." The device contains a bradycardia support system as well as a high energy defibrillation shock system to revert ventricular tachycardias to normal sinus rhythm. On reconfirmation of the presence of a tachycardia, a shock is delivered to the ventricle of a patient at a predetermined time or when the desired energy level is reached. This device is not capable of delivering atrial cardioversion in order to alleviate the condition of atrial fibrillation.

U.S. Pat. No. 4,572,191 to Mirowski et al. describes an atrial cardioverting device that is externally driven by either the physician or the patient. The detection of an arrhythmia requires the patient to recognize it, which is disadvantageous for a number of reasons including medical clinic visits, carrying expensive equipment around, or just the failure to recognize a tachycardia. Furthermore, the device is incapable of automatic detection and reconfirmation, as well as failing in the capacity to defibrillate the ventricles of a patient in the event an atrial shock accelerates the rhythm into VT/VF. This patent also describes the delivery of cardioversion shocks using a single pacing lead. A single pacing lead has been found, by recent research, to be inadequate in effectively discharging a cardioversion shock. Significantly, the main reason for this problem is that pacing leads possess a very low surface area, giving rise to a high impedance at the area of discharge. Aside from the device using too much power, the patient is subjected to a risk of tissue damage at the electrode interface.

Another problem exists with the Mirowski et al. device as there are no provisions therein for sensing R-waves and for pacing the patient's ventricle. Therefore the device is unable to synchronize the cardioversion shock to the ventricle. As a result, the unsynchronized atrial cardioversions delivered to a patient may cause VF, resulting in a further hazardous situation.

A further disadvantage of the above device is that it is turned off except when it is externally engaged by a magnet that allows the power source to charge. Thus the device is inadequate as an automatic implantable therapeutic device. Also, since the device is not capable of being instituted within a pacemaker defibrillator system, it does not have provisions for allowing bradycardia pacing, single or dual chamber antitachycardia pacing and defibrillation therapy to the ventricle. Therefore, aside from failing to adequately cardiovert the atrium successfully and automatically, the device fails as an all round therapeutic medical device offering a variety of treatments to the patient.

It is an object of the present invention to provide an improved implantable device for the automatic detection of atrial arrhythmias and for providing atrial cardioversion therapy therefor.

It is also an object of the invention to achieve effective cardioversion of atrial fibrillation with minimal power drain, and to prevent tissue damage due to high voltages being discharged over a small area, such as results from the use of a single pacing electrode.

It is a further object of the invention to provide a device having at least two defibrillation endocardial electrodes or other suitable electrodes of surface area substantially greater than that of a normal pacing lead, and of substantially lower impedance than the latter, and including at least one subcutaneous patch, which device does not require a magnet or any other external manual switching system for turning on the power source to charge its capacitor.

Another object of the invention is to provide an improved device which is on call at all times, and which is capable of being incorporated within an implantable automatic pacemaker defibrillator/cardioverter having the ability to provide defibrillation therapy to a patient's ventricle, as well as antitachycardia pacing therapy and bradycardia support pacing to either or both chambers of the heart when required.

It is yet another object of the invention to provide an automatic implantable device capable of delivering low energy cardioversion therapy into the atrium in order to improve the health and safety of patients by returning atrial arrhythmias to normal rhythms, thereby obviating the need for unnecessary high energy shocks.

A still further object of the invention is to minimize complications associated with atrial arrhythmias, since patients who have experienced atrial fibrillation have been reported to have a higher mortality rate due to embolism development.

An additional object of the invention is to provide a device which has the ability to achieve atrial cardioversion, either with R-wave synchronization or during a device-initiated ventricular refractory period, to insure that the vulnerable zone of the ventricle is avoided, thereby minimizing post-shock arrhythmias attributable to shock delivery during the ventricular vulnerable zone and degeneration of the arrhythmia into VT/VF.

It is a further object of the invention to provide an atrial cardioversion device having a plurality of electrode configurations, and having the ability to switch from one electrode configuration to another prior to the delivery of a shock or between deliveries of consecutive shocks.

Further objects and advantages of this invention will become apparent as the following description proceeds.

SUMMARY OF THE INVENTION

Briefly stated, and in accordance with one embodiment of the invention, there is provided an implantable atrial cardioverting device for the reversion of atrial tachycardias, comprising: means for storing electrical energy; means for detecting the presence of an atrial tachycardia; an electrode lead system including a plurality of electrode leads therein, each of the leads including a cardioverting electrode having a substantially larger electrode surface area and lower electrode impedance than the surface area and impedance of a pacing lead electrode, at least one of the leads being an atrial endocardial electrode lead; a plurality of atrial cardioversion electrode configurations, each of the configurations including at least two of the electrode leads; switching means responsive to the detection of an atrial tachycardia by the detecting means for selectively connecting the energy storage means to one of the atrial cardioversion electrode configuration; means for setting the level of electrical energy stored in the electrical energy storing means to an appropriate level for an atrial cardioversion shock; and, means for discharging the stored electrical energy across the selected atrial cardioversion electrode configuration.

In accordance with another aspect of the invention there is provided an implantable cardioverting/defibrillating device for the reversion of tachycardias, comprising: means for storing electrical energy; means for detecting the presence of an atrial tachycardia; means for detecting the presence of a ventricular tachycardia; an electrode lead system including a plurality of electrode leads therein, each of the leads including a cardioverting electrode having a substantially larger electrode surface area and a substantially lower electrode impedance than the surface area and impedance of a pacing lead electrode, at least a first one of the leads being an atrial endocardial electrode lead and a second one of the leads being a ventricular endocardial electrode lead; a plurality of atrial cardioversion electrode configurations, each of the configurations including at least two of the elctrode leads; a plurality of ventricular defibrillating electrode configurations, each of the configurations including at least two of the electrode leads; first switching means responsive to the detection of an atrial tachycardia by said atrial tachycardia detecting means for selectively connecting the energy storage means to one of said atrial cardioversion electrode configurations; second switching means responsive to the detection of a ventricular tachycardia by said ventricular tachycardia detecting means for selectively connecting the energy storage means to one of the ventricular defibrillating electrode configurations; means for setting the level of electrical energy stored in the electrical energy storing means to an appropriate level for atrial cardioversion shock; means for setting the level of electrical energy stored in the electrical energy storing means to an appropriate level for a ventricular defibrillation shock; and, means for discharging the stored electrical energy across a selected one of the atrial and ventricular electrode configurations. Preferably, the foregoing device also includes means for delivering atrial and ventricular bradycardia and antitachycardia pacing therapy.

In accordance with a further aspect of the invention the foregoing device may also preferably include means for sensing R-waves and delivering ventricular pacing pulses; means responsive both to the detection of an atrial tachycardia and to the absence of an R-wave during a predetermined period of time following such detection of an atrial tachycardia for delivering a ventricular pacing pulse to produce a temporary ventricular refractory condition; and means for timing the delivery of the atrial cardioversion shock to occur during such temporary refractory condition. Additionally, it may also preferably include means responsive both to the detection of an atrial tachycardia and to the detection of an R-wave during a predetermined period of time following such detection of an atrial tachycardia for timing the discharging of the stored electrical energy to synchronously occur during an absolute ventricular refractory period which occurs following the R-wave.

In accordance with another aspect of the invention there is provided a method of operating an implantable atrial tachycardia cardioverting device, the device including an electrode lead system having a plurality of electrode leads therein, each of which leads includes a cardioverting electrode having a substantially larger surface area and lower electrode impedance than the surface area and impedance of a pacing lead electrode, at least one of the leads being an atrial electrode, the device further including a plurality of atrial cardioversion electrode configurations, each of the configurations including at least two of the electrode leads, the method comprising the steps of:

A) detecting the presence of an atrial tachycardia;
B) storing a charge of electrical energy at an appropriate level for an atrial cardioversion shock;
C) connecting the stored charge of electrical energy to one of the electrode configurations;
D) delivering cardioversion shock therapy across such one of such electrode configurations;
E) determining whether the shock therapy has reverted the atrial tachycardia, and if it has not,
F) storing another charge of electrical energy at an appropriate level for an atrial cardioversion shock;
G) connecting the stored other charge of electrical energy to another one of the electrode configurations; and
H) delivering cardioversion shock therapy across such other one of the electrode configurations.

The device and method may further include provisions for antitachycardia pacing when a tachycardia is detected. The antitachycardia pacing may take the form of either a single chamber or a dual chamber algorithm such as is described in U.S. Pat. No. 4,998,974, entitled "Apparatus and method for Antitachycardia Pacing in Dual Chamber Arrhythmia Control System", to N. L. Gilli, the present inventor, which patent is assigned to the assignee of the present invention. The antitachycardia pacing is preferably issued prior to cardioversion or other treatment of a secondary arrhythmia. Also, should the atrial cardioverting shock accelerate or degenerate the arrhythmia to a VF or VT, defibrillator shock therapy is preferably available. In such a situation the device uses the switching configuration to switch to the defibrillator electrode system at an appropriate energy level. However, to prevent the occurrence of a cardioverting shock causing a ventricular arrhythmia when the ventricles are non-refractory, and in the absence of a sensed R-wave, a ventricular pace may be used just prior to the time that the shock is delivered to the atrium. If an R-wave is present, the atrial cardioversion is synchronized with it to prevent VF development. The invention is effectively achieved with endocardial defibrillating leads, or other leads in which the electrodes are much larger in surface area and lower in impedance than are the electrodes in pacing leads. Alternatively, subcutaneous defibrillation patches as well as epicardial patches, or any combination, thereof may be used in conjunction with the endocardial leads.

BRIEF DESCRIPTION OF THE DRAWINGS

Further objects, features and advantages of the invention will become apparent upon consideration of the following detailed description in conjunction with the drawings, in which:

FIG. 4A shows an electrocardiogram (ECG) of a ventricular fibrillation treated by ventricular defibrillation;

FIG. 4B shows an ECG of an atrial fibrillation treated by atrial cardioversion;

FIG. 4C shows an ECG of treatment of an atrial fibrillation by first and second atrial cardioversion attempts, wherein the first cardioversion attempt fails to revert the fibrillation and the electrode configuration is switched prior to the second cardioversion attempt;

FIG. 4D shows an ECG of a ventricular fibrillation which, after defibrillation therapy, initiates an atrial fibrillation which in turn causes atrial cardioversion to be applied;

FIG. 8 is a plan view of a ventricular endocardial lead having a cardioverting electrode and a pair of pacing electrodes therein;

FIG. 9 is a plan view of an atrial endocardial lead having a cardioverting electrode and a pair of pacing electrodes therein;

BEST MODE OF THE INVENTION

Figure 1:
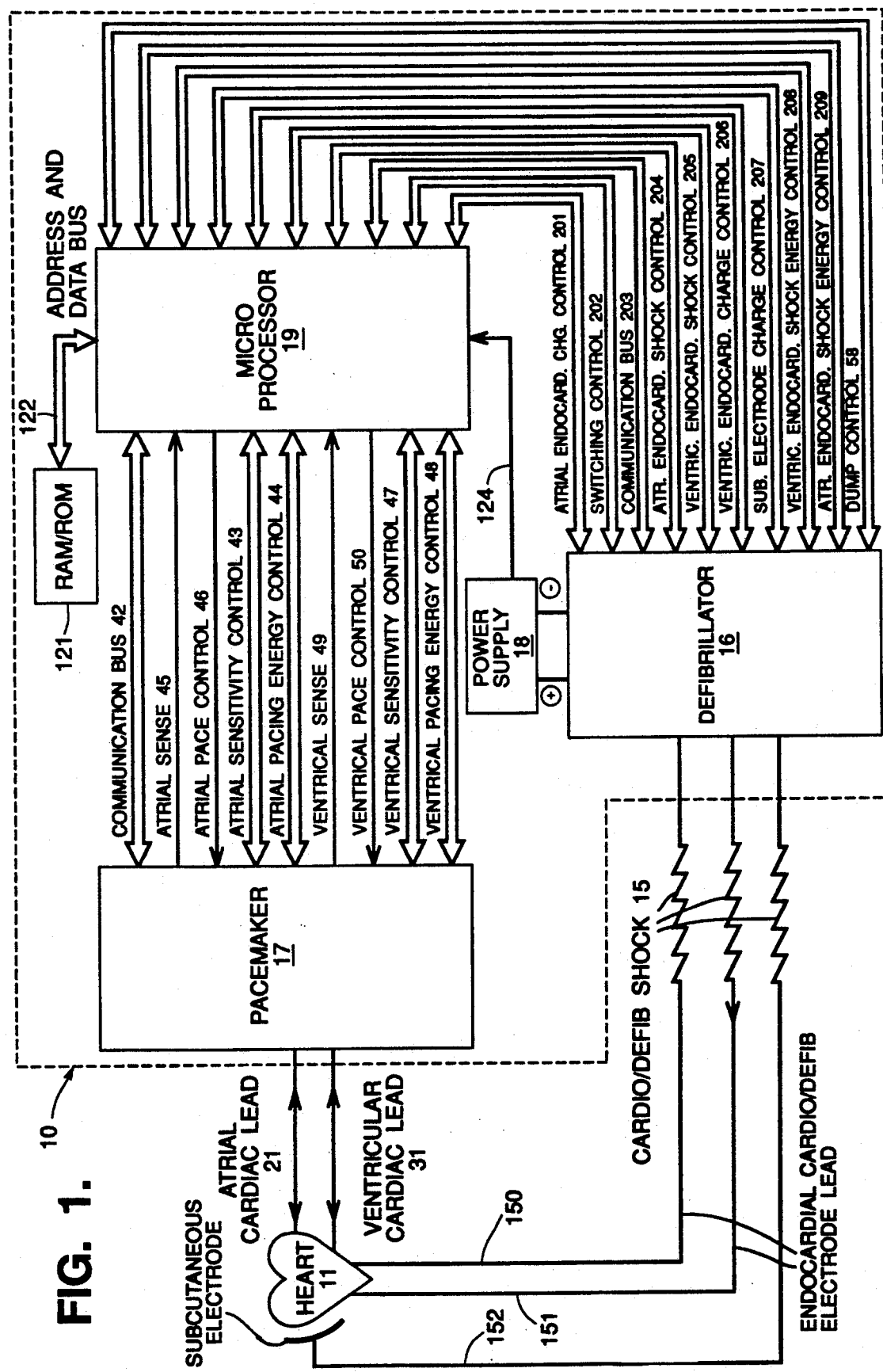
FIG. 1 depicts a block diagram of a dual chamber arrhythmia control system.

Referring to FIG. 1, there is depicted a block diagram of an implanted dual chamber arrhythmia control system or device 10, which comprises: an atrial cardiac lead 21 for sensing and pacing in the atrium and a ventricular cardiac lead 31 for sensing and pacing in the ventricle, the distal end portions of both of which are positioned in the patient's heart 11; a pacemaker 17 for the detection of analog signals representing cardiac electrical activity, and for the delivery of pacing pulses to the heart; a microprocessor 19 which, in response to various inputs received from the pacemaker 17 as well as from a defibrillator 16, performs various operations so as to generate different control and data outputs to both the pacemaker 17 and the defibrillator 16; a power supply 18 for the provision of a reliable voltage level; defibrillator 16 which produces a high voltage to charge its capacitors and then discharges them in response to control signals from the microprocessor 19; and an atrial endocardial cardioversion electrode lead 150, a ventricular endocardial defibrillation electrode lead 151 and a subcutaneous electrode lead 152, for transferring the energy of a cardioversion/defibrillator shock 15 from the implanted device 10 to either the atrium or the ventricle of the heart 11. Further details in regard to leads 150, 151 and 152 are hereinafter provided in connection with discussions of FIGS. 2A, 7A-7F, and 8-11.

A number of control signals pass between the microprocessor 19 and defibrillator 16. These control signals include an atrial endocardial charge control signal in line 201, and a switching control signal on line 202. The switching control signal on line 202 switches the defibrillator 16 (which in addition to providing ventricular defibrillation shocks also provides atrial cardioversion shocks) among various electrode configurations available to it for providing either defibrillation to the ventricles, by means of a ventricular defibrillation lead configuration (see, e.g., FIG. 7D), or cardioversion to the atrium, by means of an atrial cardioversion lead configuration (see, e.g., FIG. 7B). These lead configurations are described in greater detail hereinafter in connection with a discussion of FIGS. 7A to 7F. Other control signals passing from the microprocessor 19 to the defibrillator 16 include those on a communication bus 203, an atrial endocardial shock control signal on line 204, a ventricular endocardial shock control signal on line 205, a ventricular endocardial charge control signal on line 206, a subcutaneous electrode charge control signal on line 207, a ventricular endocardial shock energy control signal on line 208, an atrial endocardial shock energy control signal on line 209, and a dump control signal on line 58.

Figure 2A:
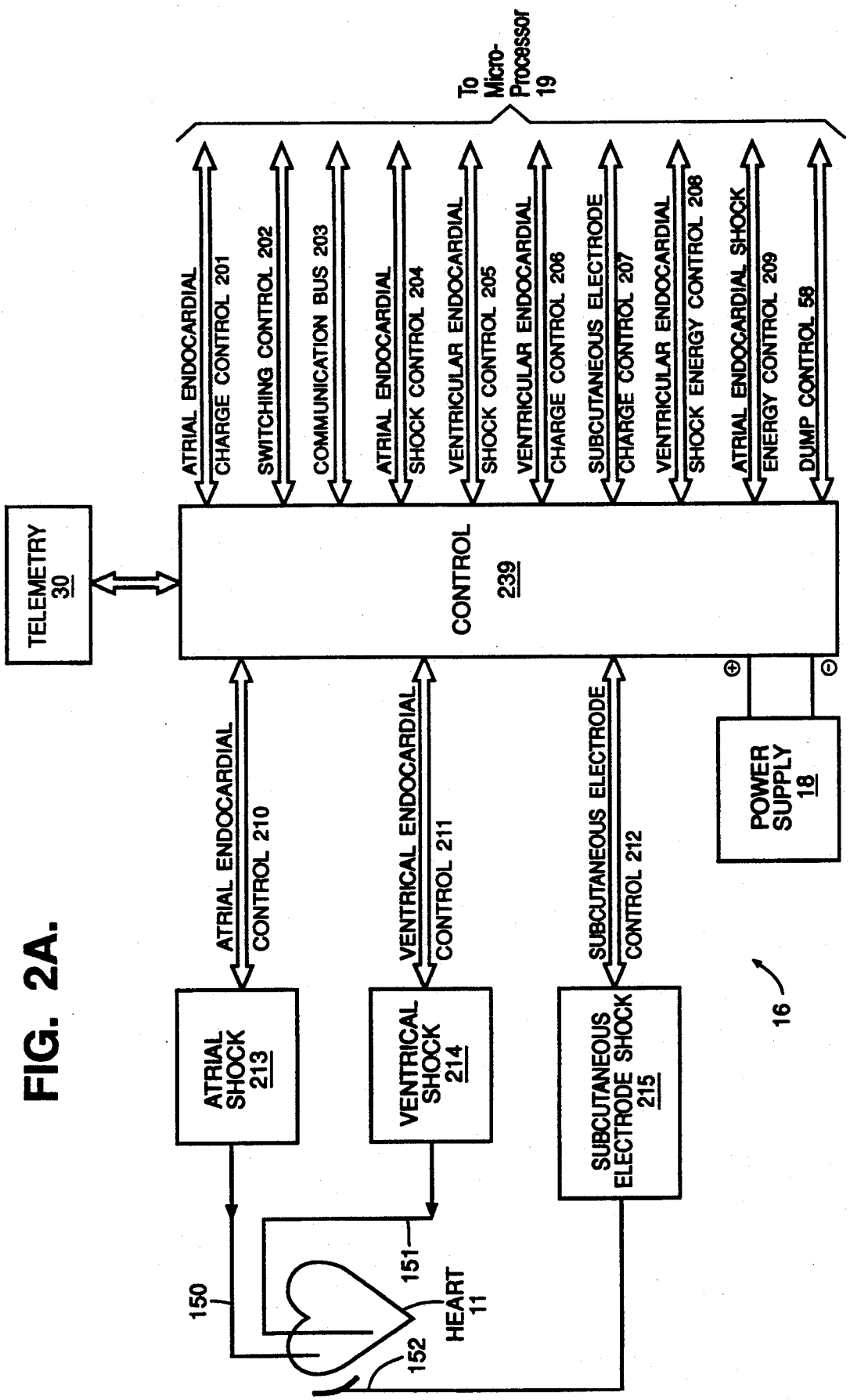
FIG. 2A depicts a block diagram of a defibrillator shown in FIG. 1.
Figure 10:
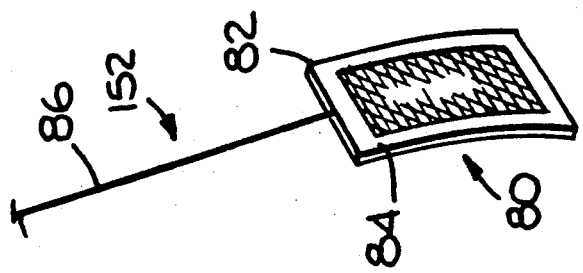
FIG. 10 is a perspective view of a subcutaneous patch electrode lead which may be used with the invention; and, FIG. 11 is a plan view, in partial cross-section, of a subcutaneous braid electrode lead which may be used with the invention.

Referring to FIG. 2A there is depicted a block diagram of the defibrillator 16 of FIG. 1. Circuitry for providing an atrial cardioversion shock is shown at 213; circuitry for providing a ventricular defibrillation shock is shown at 214; and circuitry for providing a subcutaneous electrode shock is shown at 215. The atrial endocardial lead 150 connects the atrial shock circuitry 213 to the atrium of the heart 11. The ventricular endocardial lead 151 connects the ventricular shock circuitry 214 to the ventricle of the heart 11. The subcutaneous electrode lead 152 connects the subcutaneous electrode shock circuitry 215 to a subcutaneous electrode at the distal end of lead 152. Preferably, the endocardial leads 150 and 151 and the subcutaneous electrode lead 152 are provided with large surface area, low impedance electrodes adjacent their distal ends such as the braid electrodes, described briefly herein in connection with FIGS. 8, 9 and 11, and described in greater detail in U.S. Pat. No. 5,005,587 to S. E. Scott, entitled "Braid Electrode Leads and Catheters and Methods for Using the Same," which patent is assigned to the assignee of the present invention. Alternatively, in another embodiment, the subcutaneous electrode lead 152 may be provided with a conventional patch electrode, as shown in FIG. 10.

Telemetry circuitry, shown at 30, provides a bidirectional link between a defibrillator control block 239 and an external device such as a programmer (not shown). It allows data such as the operating parameters to be read from or altered in the implanted device 10.

The defibrillator control block 239 is connected to the atrial shock circuitry 213 by means of an atrial endocardial control line 210. The control block 239 is connected to the ventricular shock circuitry 214 by means of a ventricular endocardial control line 211. The subcutaneous electrode shock circuitry 215 is connected to control block 239 by means of a subcutaneous electrode control line 212. A number of control signals pass between microprocessor 19 and defibrillator control block 239. These control signals include the aforementioned atrial endocardial charge control signal on line 201, the switching control signal on line 202, the various signals on communication bus 203, the atrial endocardial shock control signal on line 204, the ventricular endocardial shock control signal on line 205, the ventricular endocardial charge control signal on line 206, the subcutaneous electrode charge control signal on line 207, the ventricular endocardial shock energy control signal on line 208, the atrial endocardial shock energy control signal on line 209, and the dump control signal on line 58.

Figure 2B:
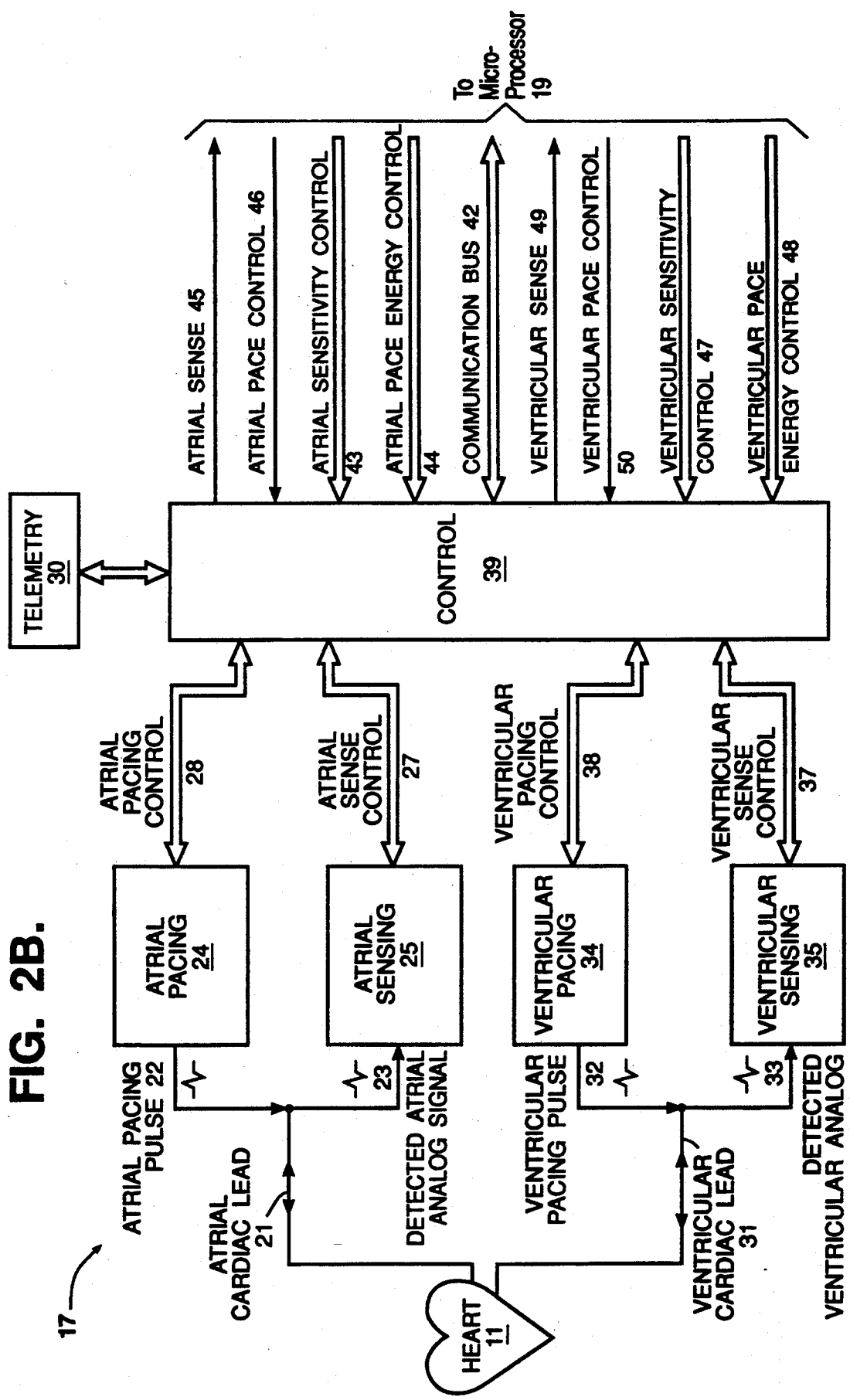
FIG. 2B depicts a block diagram of a pacemaker shown in FIG. 1.

Referring to FIG. 2B, there is depicted a block diagram of the pacemaker 17 of FIG. 1. Pacemaker 17 comprises atrial pacing circuitry 24, ventricular pacing circuitry 34, atrial sensing circuitry 25, ventricular sensing circuitry 35, and the aforementioned telemetry circuitry 30. In addition, pacemaker 17 includes a pacemaker control block 39.

In operation, the sensing circuits 25 and 35 detect atrial and ventricular analog signals 23 and 33, respectively, from the heart 11 and convert the detected signals to digital signals. The sensing circuits 25 and 35 respectively receive an input atrial sense control signal via line 27 and an input ventricular sense control signal via line 37 from the control block 39, which signals determine the sensitivity applied to the detection circuits. A change in this sensitivity will affect the voltage deviation required at the sensing electrode for a sense to be registered. The operation of the logic which changes the sensitivity is described in more detail in U.S. Pat. No. 4,940,054 to Richard Grevis and Norma L. Gilli, entitled "Apparatus and Method for Controlling Multiple Sensitivities in Arrhythmia Control System Including Post Therapy Pacing Delay."

The pacing circuits 24 and 34 also respectively receive an input atrial pacing control signal and an input atrial pacing energy control signal via line 28, and an input ventricular pacing control signal and an input ventricular pacing energy control signal via line 38, from the pacemaker control block 39. The pacing control signals determine the type of pacing to occur, while the magnitude of the pulse energy is determined by the pacing energy control signals. The operation of the logic which changes the pulse energy is described in more detail in U.S. Pat. No. 4,869,252, entitled "Apparatus and Method for Controlling Pulse Energy in Antitachyarrhythmia and Bradycardia Pacing Devices,"

to Normal L. Gilli. The pacing circuits 24 and 34 generate the atrial pacing pulse 22 and the ventricular pacing pulse 32 which are delivered to the patient's heart 11 by means of the atrial cardiac lead 21 and the ventricular cardiac lead 31, respectively.

Telemetry circuitry 30, which was discussed earlier in connection with a discussion of the defibrillator 16, also provides a bi-directional link between the pacemaker control block 39 and an external device such as a programmer (not shown). It allows data such as the operating parameters to be read from or altered in the implanted device 10.

An atrial sense signal and a ventricular sense signal pass via respective lines 45 and 49 from the pacemaker control block 39 to the microprocessor 19. Passing from the microprocessor 19 to the control block 39 are an atrial pace control signal on line 46, an atrial sensitivity control signal on line 43, an atrial pacing energy control signal on line 44, a ventricular pace control signal on line 50, a ventricular sensitivity control signal on line 47, and a ventricular pacing energy control signal on line 48. A communication bus 42 is employed for communicating various other signals between the control block 39 and the microprocessor 19.

Figure 3:
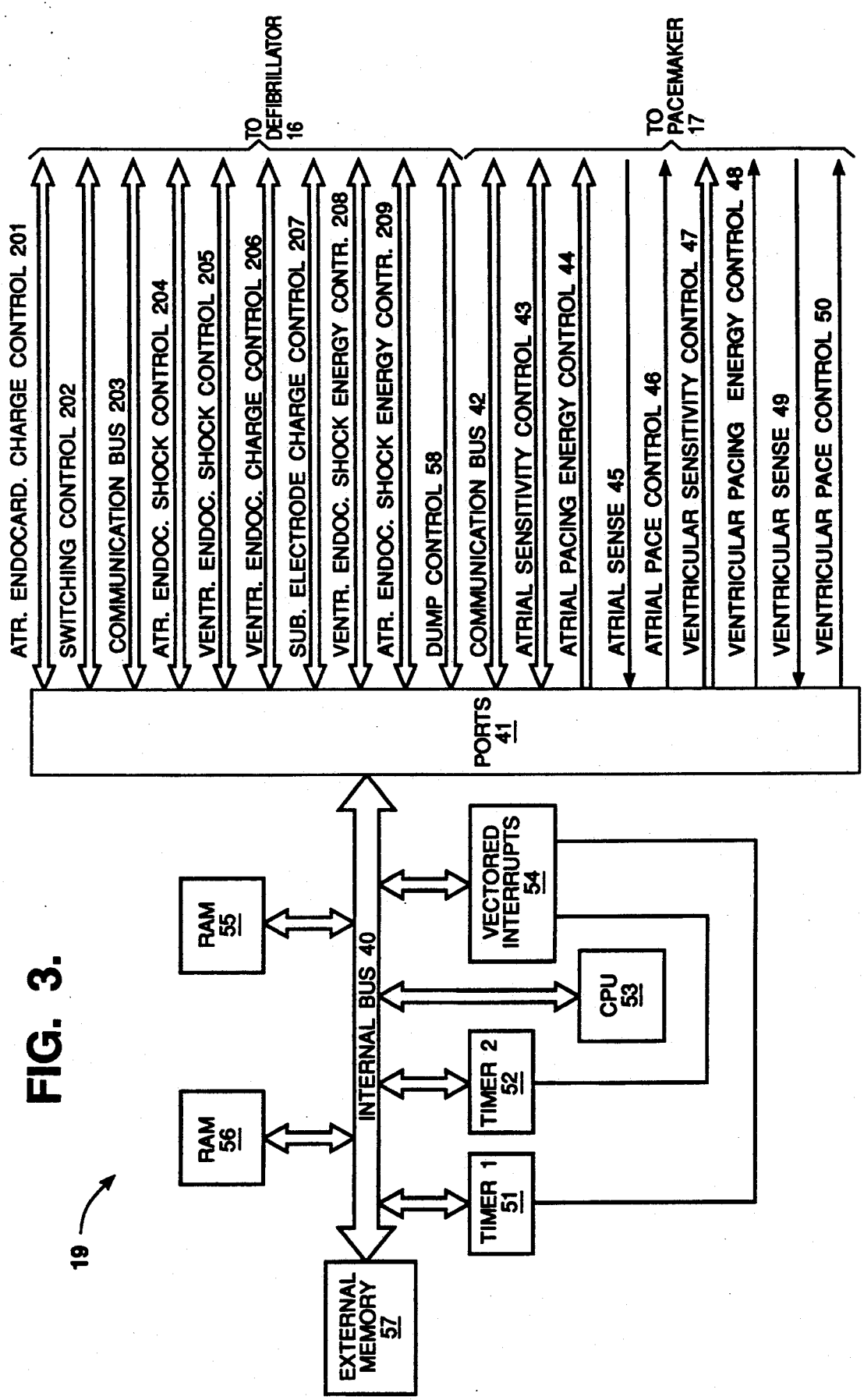
FIG. 3 depicts a block diagram of a microprocessor shown in FIG. 1.

Referring to FIG. 3, there is shown a block diagram of the microprocessor 19 of FIG. 1. It comprises two 16-bit timers 51 and 52, a central processing unit or CPU 53, a vectored interrupts block 54, a read only memory or ROM 55, a random access memory or RAM 56, an external memory 57, a ports block 41 and an internal communication bus 40.

Microprocessor 19 receives various status and/or control inputs from pacemaker 17 and defibrillator 16 such as the sense signals on lines 45 and 49, performs operations such as arrhythmia detection, and produces outputs such as the atrial pace control signal on line 46 and the ventricular pace control signal on line 50, which determine the type of pacing to take place. Other control outputs generated by microprocessor 19 include the atrial and ventricular pacing energy control signals on respective lines 44 and 48 which determine the magnitude of the pulse energy, the dump control signal on line 58 which indicates that a shock is to be dumped at an internal load within the defibrillator, and the various charge control signals on lines 201, 206, and 207 which determine the voltage level of the shock to be delivered. Other output signals pass from microprocessor 19 to the defibrillator control block 239. These control signals, mentioned earlier herein, include the switching control signal on line 202, the various signals on communication bus 203, the atrial endocardial shock control signal on line 204, the ventricular endocardial shock control signal on line 205, the ventricular endocardial shock energy control signal on line 208, and the atrial endocardial shock energy control signal on line 209. Other control outputs from the microprocessor include the atrial and ventricular sensitivity control signals on lines 43 and 47, respectively, which determine the sensitivity settings of the pacemaker sensing circuits.

Referring to FIG. 4A in conjunction with FIG. 1, there is depicted an electrocardiogram or ECG trace outlining the application of the device 10 in treating a VF, shown at 180. The device 10 charges a capacitor (not shown) in defibrillator 16 to an appropriate high energy level for defibrillation, switches to a programmed electrode configuration (e.g. the configuration of FIG. 7D) and delivers a defibrillation shock 181 to the ventricle of the patient's heart 11. Normal sinus rhythm (NSR) 182 results, indicating effective therapy.

Referring to FIG. 4B in conjunction with FIG. 1, there is depicted an ECG trace outlining a low energy cardioversion shock sequence of device 10. As shown, an AF has developed at 183. Prior to the delivery of low energy cardioversion shock therapy at 185, the device switches to a programmed electrode configuration at 184 (e.g., the configuration of FIG. 7A) and checks for the presence of R-waves in the ventricle. The capacitor (not shown) in defibrillator 16 is charged to an appropriate low energy level for atrial cardioversion and when ready to deliver, it waits for a programmable time period such as a normal pacing standby interval of 857 ms. If during this time an R-wave is not detected, then prior to the atrial cardioversion shock, a pacing pulse is delivered to the ventricle. The timing of the pacing pulse is such that it renders the ventricle depolarized during the subsequent delivery of the low energy shock. The interval between the delivery of the ventricular pacing pulse and the delivery of the shock is usually short. In the preferred embodiment, this interval is 100 ms but it may be longer or shorter than this value provided that the ventricle is depolarized at the time of delivery of the low energy cardioversion shock. If during the 857 ms standby period an R-wave is detected, then the cardioversion therapy is delivered within 100 ms. This results in a synchronized atrial cardioversion (i.e., it is synchronized with the last inherent R-wave) so that at the moment of delivery the ventricles are refractory. This has the purpose of preventing VF's from developing. As shown, the cardioversion shock at 185 has succeeded in reverting the atrial arrhythmia, and normal sinus rhythm 186 is now present in the patient.

Referring to FIG. 4C in conjunction with FIG. 1, there is depicted an ECG trace outlining another low energy cardioversion shock sequence of device 10. As shown, an AF has developed at 187. As described with reference to FIG. 4B, and assuming the device is in a first programmed electrode configuration (e.g., the configuration of FIG. 7A), a check is made for R-waves and a pacing pulse is delivered to the ventricle 100 ms prior to the delivery of low energy cardioversion shock therapy at 188. The ventricular pacing pulse renders the ventricle depolarized during the subsequent delivery of the cardioversion shock. Following cardioversion shock delivery, an AF is still shown to be present at 189, with reconfirmation of the AF shown at 190. At this point, as shown at 191, there is a change or switch in the electrode configuration, according to programmed instructions and the electrode configuration combinations available, to a second programmed electrode configuration (e.g., the configuration of FIG. 7B). As described with reference to FIG. 4B, and above, a test for R-waves again occurs and within 100 ms of detection of the R-wave, a cardioversion shock is delivered, at 192, utilizing the changed electrode configuration to improve cardioversion effectiveness. Reversion of the atrial fibrillation and resultant establishment of normal sinus rhythm is shown at 193.

Referring to FIG. 4D in conjunction with FIG. 1, there is depicted an ECG trace outlining a VF 194 for which a high energy defibrillation shock 195 is delivered in an attempt to revert the VF. Although the high energy shock 195 in this instance has successfully reverted the ventricular fibrillation, utilizing the electrode configuration of FIG. 7D for example, an atrial fibrillation 196 has developed post-shock. The AF is reconfirmed at 197. A change in the electrode switching configuration is then given at 198 (e.g. to the electrode configuration of FIG. 7B), and atrial cardioversion therapy is applied at 199. The AF is shown as having been successfully reverted to normal sinus rhythm at 200.

Figure 5:
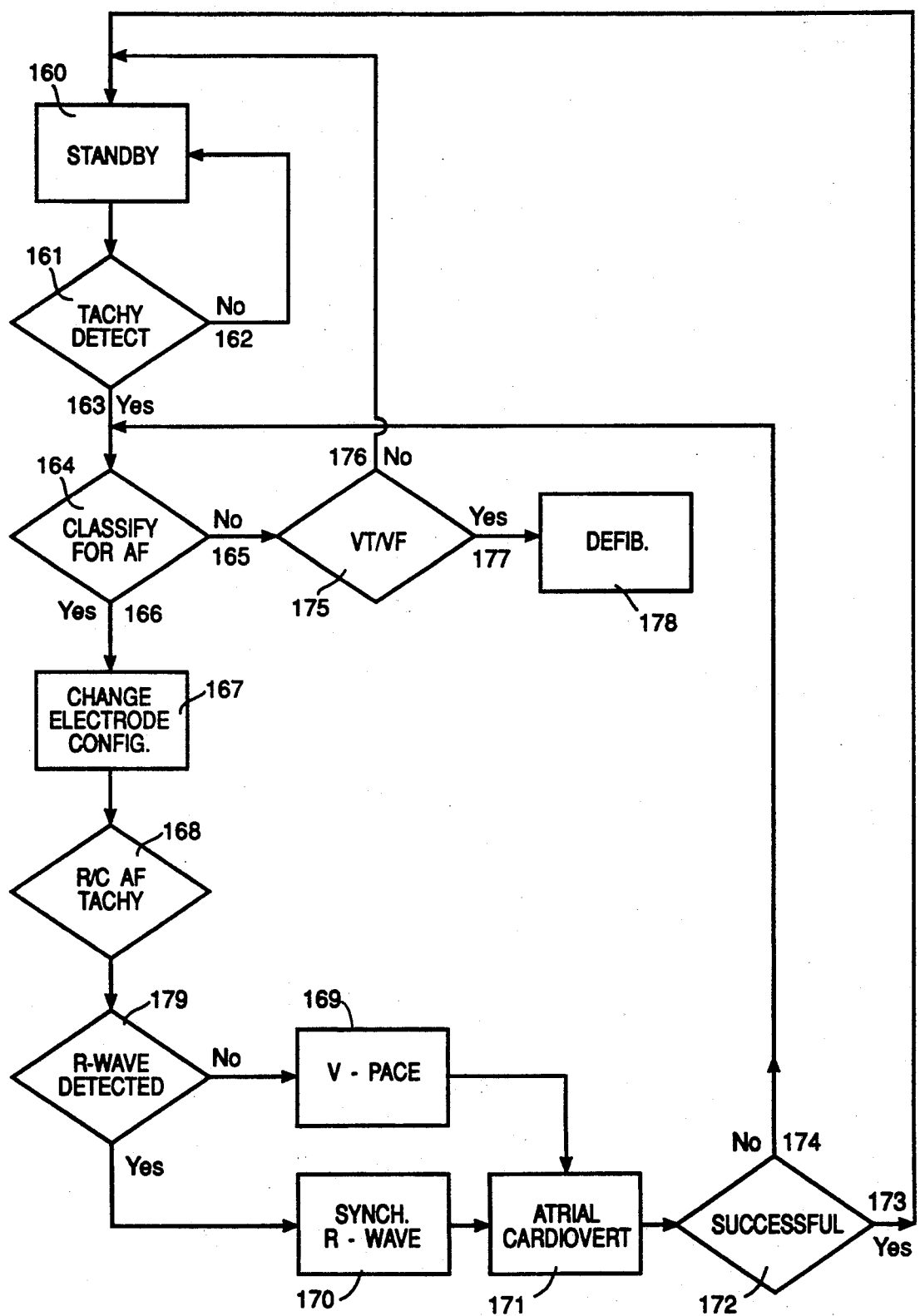
FIG. 5 depicts a flow diagram of the treatment of atrial fibrillation in a dual chamber arrhythmia control system according to the invention.

Referring now to FIG. 5 there is depicted a flow chart showing the sequence of events occurring during operation of the implantable arrhythmia control system. The start or standby mode is shown at block 160. A tachycardia detection decision occurs at block 161. If no tachycardia is present, as indicated at 162, there is a return to the standby mode of block 160. If a tachycardia is detected, as indicated at 163, it is examined to determine whether or not it is an AF at block 164. If it is not an AF, as indicated at 165, then it is examined to determine whether or not it is a VT/VF at block 175. If it is not a VT/VF, as indicated at 176, there is a return to the standby mode of block 160. If a VT/VF is present, as indicated at 177, then at block 178 defibrillation therapy is applied by the device to the ventricle of the patient.

Figure 7A:
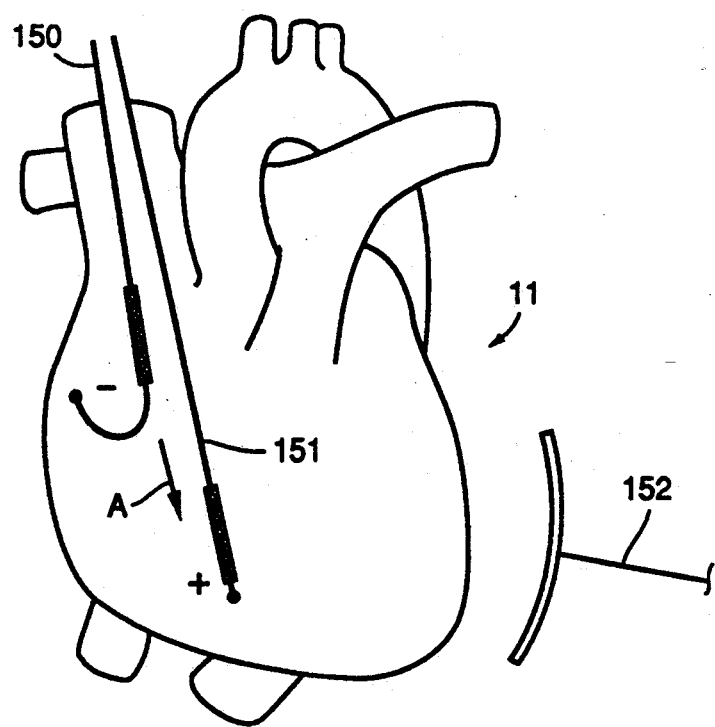
FIG. 7A depicts a unidirectional lead configuration according to the invention.
Figure 7B:
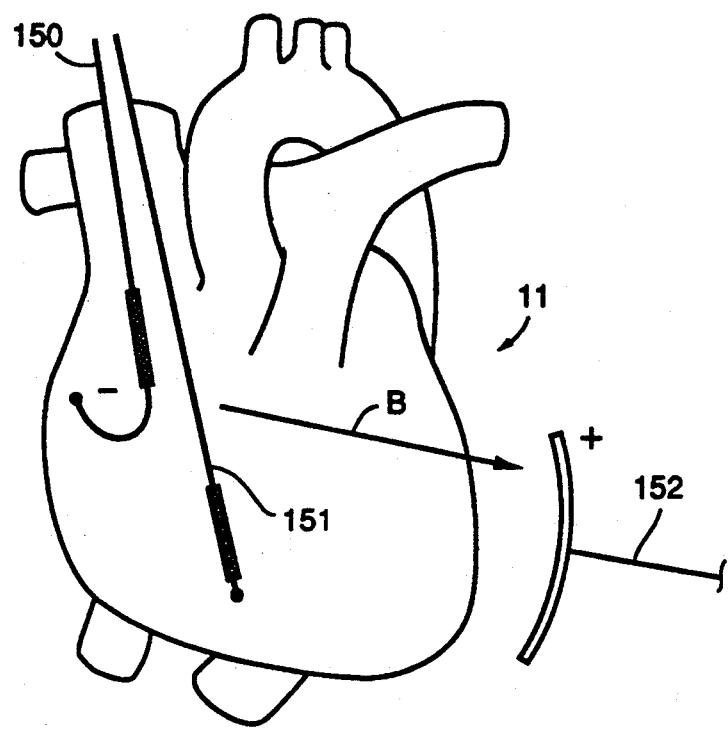
FIG. 7B depicts a further unidirectional lead configuration according to the invention.
Figure 7C:
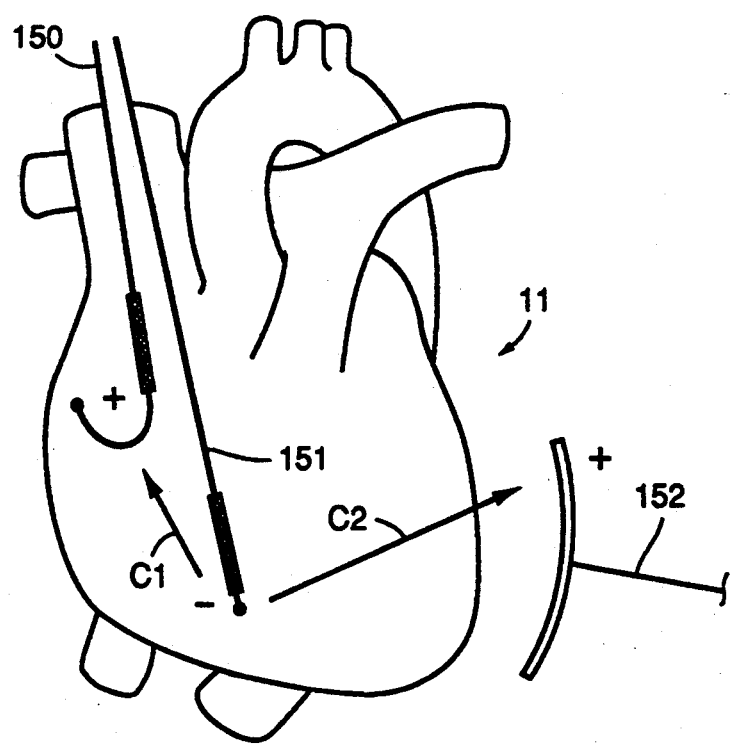
FIG. 7C depicts a bidirectional lead configuration according to the invention.
Figure 7D:
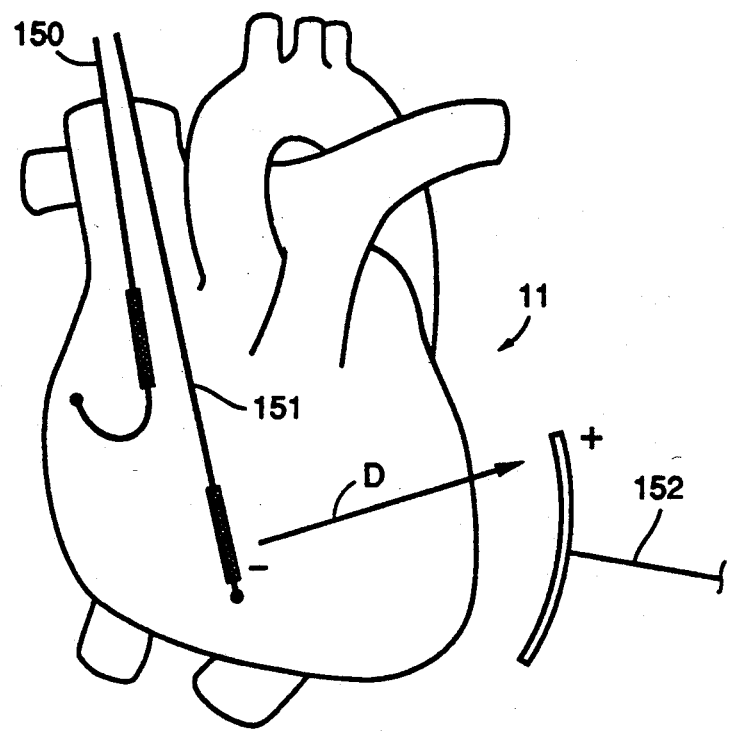
FIG. 7D depicts another unidirectional lead configuration according to the invention.

In the particular embodiment illustrated in FIG. 5, there is only one electrode configuration available at block 178 for defibrillating the ventricles, and that is the one shown in FIG. 7D. Thus the device automatically switches to this configuration at VT/VF detection. Hence, there is no need to pass via block 167, which specifically relates to changing electrode configurations in connection with atrial cardioversion. If an AF is classified at block 164, as indicated at 166, then the electrode configuration is switched to the appropriate setting at block 167. At block 168, the AF is reconfirmed.

When the device is ready to deliver a cardioversion shock, it waits at block 179 for a programmed standby interval such as 857 ms to detect the presence of an R-wave. If no R-wave is detected during the programmed standby interval, then a ventricular pace is provided by the device at block 169 to depolarize the ventricle at a programmed time interval such as 100 ms before the shock is delivered. If an R-wave is detected during the programmed standby interval, then at block 170 the device synchronizes the shock delivery with the patient's R-wave and, within 100 ms of the R-wave, delivers the atrial cardioversion therapy at block 171.

At block 172, the device checks for the success of the therapy. If successful, as shown at 173, there is a return to the standby mode of block 160. If the cardioversion therapy is not successful, as shown at 174, there is a return to the AF classifier at block 164. If an AF is still present at block 166, there is a change in the electrode configuration at block 167 and a repeat of cardioversion therapy with the new electrode configuration.

Figure 6:
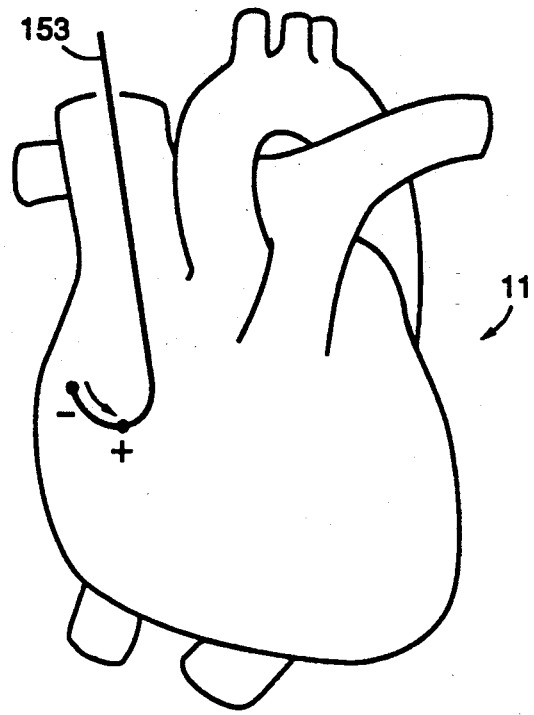
FIG. 6 shows a prior art lead configuration in an externally controlled atrial cardioverter.

FIG. 6 shows a prior art lead configuration for an externally controlled atrial cardioverting device (not shown). It comprises a two-electrode single pacing lead 153 positioned in the atrium of the heart 11, as shown.

FIG. 7A depicts a unidirectional lead configuration according to the invention, including atrial endocardial J-lead 150 in the atrium, ventricular endocardial lead 151 in the ventricle and subcutaneous electrode lead 152. In this configuration the atrial endocardial lead 150 is charged negatively and the endocardial ventricular lead 151 is charged positively. No charge is applied to the subcutaneous electrode lead 152. Thus, at delivery there is a unidirectional discharge with the waveform direction as shown by arrow A, from the electrode of atrial lead 150 to the electrode of ventricular lead 151.

FIG. 7B depicts a further unidirectional lead configuration according to the invention, including atrial endocardial lead 150 in the atrium, ventricular endocardial lead 151 in the ventricle and subcutaneous electrode lead 152. In this configuration the atrial endocardial lead 150 is charged positively, the endocardial ventricular lead 151 is uncharged, and a positive charge is applied to the subcutaneous electrode lead 152. Thus, at delivery there is a unidirectional discharge with the waveform direction as shown by arrow B, from the electrode of ventricular lead 151 to the electrode of subcutaneous electrode lead 152.

FIG. 7C depicts a bidirectional lead configuration according to the invention, including atrial endocardial lead 150 in the atrium, ventricular endocardial lead 151 in the ventricle and subcutaneous electrode lead 152. In this configuration the atrial endocardial lead 150 is charged positively, the ventricular endocardial lead 151 is charged negatively and a positive charge is applied to the subcutaneous electrode lead 152. Thus, at delivery there is a bidirectional discharge with the waveform directions as shown by arrows C1 and C2, from the electrode of ventricular lead 151 to both the electrode of atrial lead 150 and the electrode of subcutaneous electrode lead 152, respectively.

FIG. 7D depicts a further unidirectional lead configuration according to the invention, including atrial endocardial lead 150 in the atrium, ventricular endocardial lead 151 in the ventricle and subcutaneous electrode lead 152. In this configuration the atrial endocardial lead 150 is uncharged, the endocardial ventricular lead 151 is charged negatively and a positive charge is applied to the subcutaneous electrode lead 152. Thus, at delivery there is a unidirectional discharge with the waveform direction as shown by arrow D, from the electrode of ventricular lead 151 to the electrode of subcutaneous electrode lead 152.

The electrode configuration of FIG. 7D is suitably used in the preferred embodiment for defibrillation therapy to the ventricle in the case of VT. The device switches to this electrode configuration by means of a switching control signal sent from microprocessor 19 to defibrillator 16 on line 202 (FIG. 1), and the energy of the shock to be delivered is adjusted to the higher energy required for defibrillation by means of a ventricular endocardial shock energy control signal and a subcutaneous electrode charge control signal sent from microprocessor 19 to defibrillator 16 on lines 208 and 207, respectively.

Figure 7E:
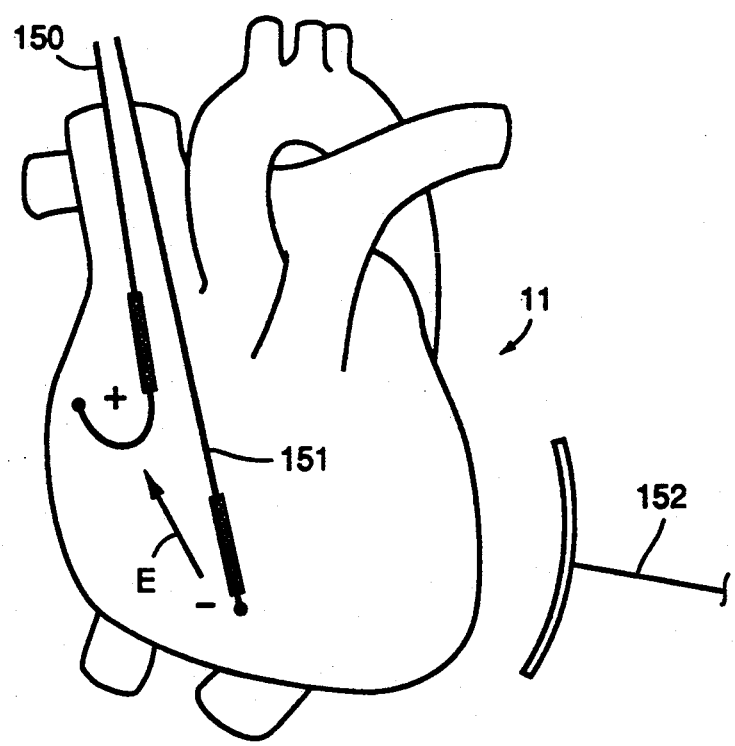
FIG. 7E depicts a still further unidirectional lead configuration according to the invention.

FIG. 7E depicts a further unidirectional lead configuration according to the invention, including atrial endocardial lead 150 in the atrium, ventricular endocardial lead 151 in the ventricle, and subcutaneous electrode lead 152. In this configuration the atrial endocardial lead 150 is charged positively, the endocardial ventricular lead 151 is charged negatively and no charge is applied to the subcutaneous electrode lead 152. Thus, at delivery there is a unidirectional discharge with the waveform direction as shown by arrow E, from the electrode of ventricular lead 151 to the electrode of atrial lead 150.

Figure 7F:
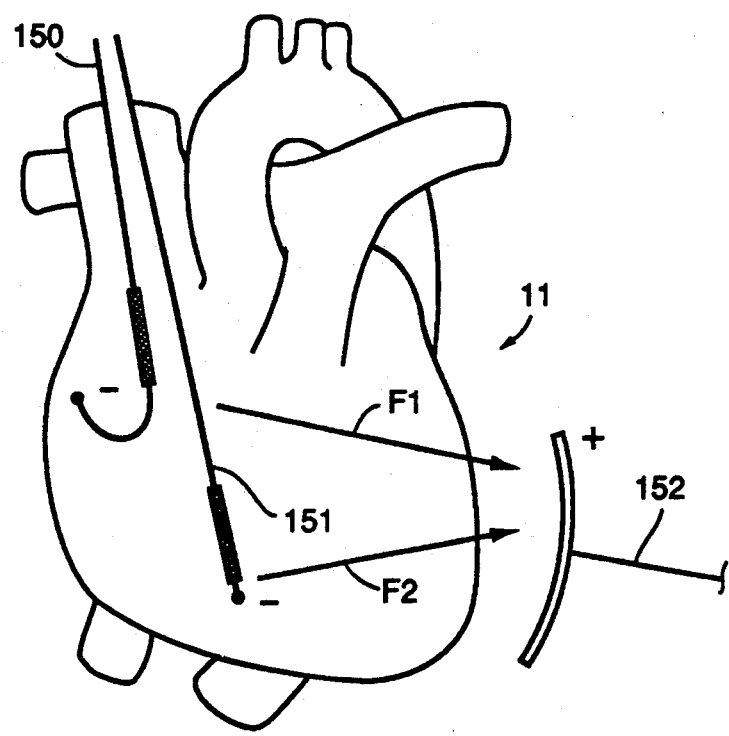
FIG. 7F depicts another bidirectional lead configuration according to the invention.

FIG. 7F depicts another bidirectional lead configuration according to the invention, including atrial endocardial lead 150 in the atrium, ventricular endocardial lead 151 in the ventricle and subcutaneous electrode lead 152. In this configuration the atrial endocardial lead 150 is charged negatively, the ventricular endocardial lead 151 is charged negatively and a positive charge is applied to the subcutaneous electrode lead 152. Thus, at delivery there is a bidirectional discharge with the waveform directions as shown by arrows F1 and F2, from the electrodes both of atrial lead 150 and ventricular lead 151, respectively, to the electrode of subtaneous electrode lead 152.

Referring to FIG. 8, a ventricular endocardial defibrillation electrode lead 151 that may be used in connection with the present invention has there been illustrated as part of a tripolar endocardial ventricular defibrillation and pacing catheter or lead 110. Lead 110 includes a conventional tip assembly 112 having a distal tip electrode 114 and a band or ring electrode 116 for pacing and sensing, as is well known in the art. As is also well known, tip electrode 114 and ring electrode 116 may be formed of a 90% platinum-10% iridium alloy covered with porous platinum. The lead 110 comprises a polyurethane tube having two small lumens and one large lumen (not shown) therein.

Electrical connection is made to tip electrode 114 and ring electrode 116 by two separate wire conductors (not shown). Each conductor extends along the length of one of the lumens of lead 110 and terminates in a connector 126 of a type well known in the art. Connector 126 includes pins 128 and 130 which are electrically connected to terminals 114 and 116, respectively, by the aforesaid conductors. The pins 128 and 130 are received in the neck (not shown) of the implanted device 10 (FIG. 1) and, together with the aforesaid conductors, comprise the ventricular cardiac lead 31 that connects to the pacemaker 17 of FIG. 1 for providing ventricular pacing stimulation to the heart and for receiving sensed ventricular signals therefrom.

Lead 110 includes a hub or a Y connector 132 from which separate polyurethane tubes 134 and 136 extend to connector 126. The aforesaid wire conductors extend through hub 132 and then through respective tubes 134 and 136, thus providing electrical connection to corresponding ones of pins 128 and 130.

Lead 110 has placed, externally along a portion of its length, a cylindrical, braid, cardioverting electrode 142. Electrical connection to electrode 142 is made by collapsing that portion of the braid not used as part of electrode 142 into a rope (not shown), and passing the rope through a small opening into the large lumen of the lead 110. This rope conductor extends into an insulating tube 138 having a first end terminating in hub 132 and a second end terminating in a defibrillator connector 140. The connector 140 has a connection pin 144 extending therefrom. Connection pin 144 is electrically connected to the end of the rope conductor and is received in the neck (not shown) of the device 10 (FIG. 1). The rope conductor, connector 140 and pin 144 constitute the lead 151 which connects to the defibrillator 16 (FIG. 1) for conducting endocardial cardioverting/defibrillating shocks 15 to the ventricle of the heart. As is apparent from an inspection of FIG. 8, the cardioverting/defibrillating electrode 142 has a substantially larger electrode surface area, and consequently a lower electrode impedance, than the surface area and impedance of pacing lead electrodes 114 and 116. This facilitates the transmission of the cardioversion shock therapy to the heart.

Referring now to FIG. 9, an atrial endocardial cardioverting lead 150 has there been illustrated as part of a J-type tripolar endocardial atrial cardioverting and pacing catheter or lead 110A. Lead 110A is generally similar to lead 110 of FIG. 8 and includes a tip assembly 112A having a pacing tip electrode 114A and a pacing ring electrode 116A. The lead 110A includes a polyurethane tube having two small lumens and one large lumen. Electrical connection is made to tip electrode 114A and ring electrode 116A by two separate wire conductors (not shown) each of which extends along the length of one of the lumens of lead 110A and terminates in a connector 126A having pins 128A and 130A which are electrically connected to terminals 114A and 116A, respectively, by the aforesaid conductors. The pins 128A and 130A are received by the pacemaker 17 (FIG. 1) and, together with the aforesaid conductors, constitute the atrial cardiac lead 21 of FIG. 1 that connects to the pacemaker 17 of FIG. 1 for providing atrial pacing stimulation to the heart and for receiving sensed atrial signals therefrom.

As in the case of the lead 110 of FIG. 8, lead 110A of FIG. 9 includes a hub or Y-connector 132A from which separate polyurethane tubes 134A and 136A extend to connector 126A. The aforesaid wire conductors extend through hub 132A and then through respective tubes 134A and 136A, thus providing electrical connection to corresponding ones of the pins 128A and 130A.

As before, lead 110A has placed, externally along a portion of its length, a cylindrical, braid, cardioverting electrode 142A. Electrical connection to electrode 142A is made by collapsing that portion of the braid not used as part of electrode 142A into a rope (not shown), and passing the rope through a small opening into the large lumen of the lead 110A. This rope conductor extends into an insulating tube 138A having a first end terminating in hub 132A and a second end terminating in a defibrillator connector 140A. Connector 140A has a connection pin 144A extending therefrom. Connection pin 144A is electrically connected to the end of the rope conductor and is received in the neck (not shown) of the device 10 (FIG. 1). The rope conductor, connector 140A and pin 144A constitute the lead 150 which connects to the defibrillator 16 (FIG. 1) for conducting endocardial cardioverting/defibrillating shocks 15 to the atrium of the heart.

As in the case of the cardioverting electrode 142 of FIG. 8, the cardioverting electrode 142A of FIG. 9 has a substantially larger surface area, and consequently a lower electrode impedance, than the surface area and impedance of pacing lead electrodes 114A and 116A. This facilitates the transmission of the cardioversion shock therapy to the heart.

Figure 11:
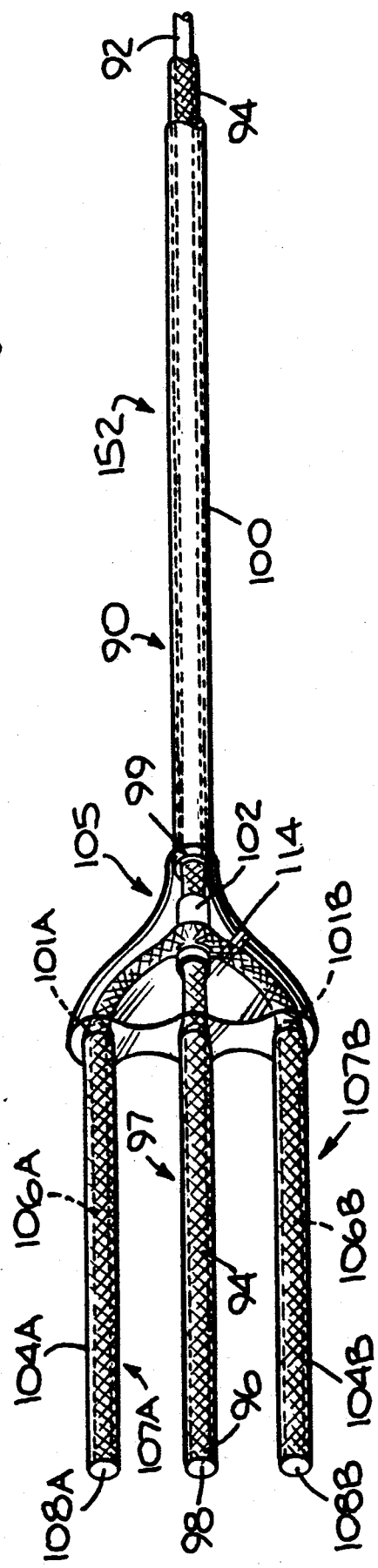

Referring now to FIG. 11, a subcutaneous electrode lead 152 having a preferred form of multi-element, braided electrode, shown generally at 90, has there been illustrated. An inner tube 92 of, for example, polyurethane material is surrounded by a cylindrical braid 94 which extends to a distal end 96 of the tube to form a finger 97. Inner tube 92 and braid 94 are terminated by a polyurethane cap 98 which is provided with a reduced diameter plug portion (not shown) that fits into the distal end 96 of tube 92 and is adhered in place by a suitable medical adhesive. An outer insulating tube 100, for example of polyurethane, fits snugly about the proximal portion of braid 94.

The proximal ends of each of two braids 104A and 104B are cut to dimensions slightly longer than the distance from distal end 96 to connecting sleeve 102 and are wrapped about and braised to metallic sleeve 102. Braising is used so as to firmly mechanically and electrically connect braid 94, metallic sleeve 102, braid 104A and braid 104B to one another.

Respective tubes 106A and 106B, preferably formed of the same material as inner tube 92 and having a length somewhat shorter than the distance from distal end 96 to connecting sleeve 102, are fitted within braids 104A and 104B, respectively, to form fingers 107A and 107B of stiffness comparable to that of finger 97.

The distal ends of fingers 107A and 107B are terminated by caps 108A and 108B, respectively, in the same manner as described above in connection with cap 98 and tube 92. A portion of the lead 90, including the distal end 99 of outer tube 100, extends distally to a region 105. Collapsed portions of braid 104A and 104B extend past the proximal ends of tubes 106A and 106B, and therefore past the proximal ends 101A and 101B of fingers 107A and 107B. These components are all held in a mold (not shown), during manufacture, having a cavity into which polyurathane material is placed so as to form a trifurcation 103. The fingers 97, 107A and 107B have lateral spacing between them so that they may be fitted into adjacent intercostal spaces. To this end, a small taper angle may be established between outer tube 100 and fingers 107A and 107B.

Although a multi-fingered subcutaneous braided electrode 90 has been illustrated in FIG. 11, it is to be understood that one or more single-fingered subcutaneous braided electrodes could be utilized in practicing the invention, or that more than one of such multi-fingered subcutaneous electrodes can be employed in utilizing this invention. In use, these electrodes are positioned subcutaneously, outside the chest cavity, in proximity to the heart.

Referring now to FIG. 10, an alternative embodiment of a subcutaneous electrode lead 152 has there been illustrated. The electrode lead 152 in this embodiment is provided with a subcutaneous patch electrode 80 having an insulated back 82 and an active wire mesh electrode face 84. An insulated electrical conductor 86 extends from patch electrode 80 and terminates at a defibrillation connector (not shown), similar to connector 140 of FIG. 8 and having a pin similar to pin 144 of FIG. 8 extending therefrom. The insulated electrical conductor 86 constitutes a portion of the subcutaneous electrode lead 152 in the embodiment of FIG. 10.

It will be apparent from the foregoing description that the present invention provides an improved implantable device both for the automatic detection of atrial arrhythmias, and for providing low energy atrial cardioversion therapy for such arrhythmias with minimal tissue damage and power drain. The invention is capable of being incoporated within an implantable automatic pacemaker defibrillator/cardioverter having the ability to provide high energy ventricular defibrillation therapy, as well as antitachycardia pacing therapy and bradycardia support pacing to either or both chambers of the heart when required.

Although the invention has been described herein with reference to particular embodiments, it is to be understood that such embodiments are merely illustrative of the application of the principles of the invention. For example, the delivery of a cardioversion shock following the detection of an atrial arrhythmia may be immediate, or it may be dependent on the charge time of the capacitor. Also shock waveforms may be monophasic, biphasic, multiphasic, or may have any waveform known in the art of pacing and defibrillating. Alternatively, the time to the delivery of a shock may depend on the hemodynamic condition of the patient, as described in U.S. Pat. No. 4,895,151 to R. Grevis et al., entitled "Apparatus and Method for Therapy Adjustment in Implantable Cardioverter." The device of the invention may also include means for delivering antitachycardia and/or bradycardia pacing therapy to either the atrium, or the ventricle, or to both the atrium and the ventricle. Hence numerous modifications may be made and other arrangements may be devised without departing from the true spirit and scope of the invention.

What is claimed is:

1. An implantable atrial cardioverting device for the reversion of atrial tachycardias, comprising:
    means for storing electrical energy;
    means for detecting the presence of an atrial tachycardia;
    an electrode lead system including a plurality of electrode leads therein, each of said leads including a cardioverting electrode having a substantially larger surface area and lower electrode impedance than the surface area and impedance of a pacing lead electrode, at least one of said leads being an atrial endocardial electrode lead;
    a plurality of atrial cardioversion electrode configurations, each of said configurations including at least two of said electrode leads;
    switching means responsive to the detection of an atrial tachycardia by said detecting means for selectively connecting said energy storage means to one of said atrial cardioversion electrode configurations;
    means for setting the level of electrical energy stored in said electrical energy storing means to an appropriate level for an atrial cardioversion shock; and,
    means for discharging said stored electrical energy across said selected atrial cardioversion electrode configuration.

2. An implantable atrial cardioverting device according to claim 1, wherein at least one of said electrode leads is a subcutaneous electrode lead, and wherein at least one of said atrial cardioversion electrode configurations includes the electrode of said subcutaneous electrode lead and the electrode of said atrial endocardial electrode lead.

3. An implantable atrial cardioverting device according to claim 2, wherein the electrode of said atrial endocardial electrode lead is negatively charged and the electrode of said subcutaneous electrode lead is positively charged when said discharging means discharges said stored electrical energy across said selected cardioversion configuration, so that a unidirectional wavefront passes through said electrode configuration.

4. An implantable atrial cardioverting device according to claim 2, wherein the electrode of said subcutaneous electrode lead is a braid electrode, wherein the electrode of said atrial endocardial electrode lead is negatively charged and the braid electrode of said subcutaneous electrode led is positively charged when said discharging means discharges said stored electrical energy across said selected cardioversion configuration, so that a unidirectional wavefront passes through said electrode configuration.

5. An implantable atrial cardioverting device according to claim 2, further including
    means for sensing R-waves and delivering ventricular pacing pulses;

means responsive both to the detection of an atrial tachycardia and to the absence of an R-wave during a predetermined period of time following such detection for delivering a ventricular pacing pulse to produce an absolute ventricular refractory condition; and, means for timing the delivery of said atrial cardioversion shock to occur during said absolute ventricular refractory condition.

6. An implantable atrial cardioverting device according to claim 5, further including means responsive both to the detection of an atrial tachycardia and to the detection of an R-wave during a predetermined period of time following such detection for timing the discharging of said stored electrical energy to synchronously occur during a ventricular refractory period which occurs following the R-wave.

7. An implantable atrial cardioverting device according to claim 1, wherein at least one of said electrode leads is a ventricular endocardial electrode lead, and wherein at least one of said atrial cardioversion electrode configurations includes the electrodes of both said atrial endocardial electrode lead and said ventricular endocardial electrode lead.

8. An implantable atrial cardioverting device according to claim 7, wherein the electrode of said atrial endocardial lead is negatively charged and the electrode of said ventricular endocardial electrode lead is positively charged when said discharging means discharges said stored electrical energy across said selected cardioversion electrode configuration, so that a unidirectional wavefront passes through said electrode configuration.

9. An implantable atrial cardioverting device according to claim 7, wherein the electrode of said atrial endocardial electrode lead is positively charged and the electrode of said ventricular endocardial electrode lead is negatively charged when said discharging means discharges said stored electrical energy across said selected cardioversion electrode configuration, so that a unidirectional wavefront passes through said electrode configuration.

10. An implantable atrial cardioverting device according to claim 1, wherein the electrode of said atrial endocardial electrode lead is positively charged and the electrode of the other of said leads is negatively charged when said discharging means discharges said stored electrical energy across said selected cardioversion configuration, so that a unidirectional wavefront passes through said electrode configuration.

11. An implantable atrial cardioverting device according to claim 1, wherein the electrode of said atrial endocardial electrode lead is negatively charged and the electrode of the other of said leads is positively charged when said discharging means discharges said stored electrical energy across said selected cardioversion configuration, so that a unidirectional wavefront passes through said electrode configuration.

12. An implantable atrial cardioverting device according to claim 1, wherein said electrode lead system includes three electrode leads therein, wherein one of said electrode leads is a subcutaneous electrode lead, wherein one of said electrode leads is a ventricular endocardial electrode lead, and wherein at least one of said atrial cardioversion electrode configurations includes the electrodes of each of said atrial endocardial electrode lead, said subcutaneous electrode lead and said ventricular endocardial electrode lead.

13. An implantable atrial cardioverting device according to claim 12, wherein the electrode of said atrial endocardial electrode lead is negatively charged, the electrode of said ventricular endocardial electrode lead is positively charged and the electrode of said subcutaneous electrode lead is uncharged when said discharge means discharges said stored electrical energy across said selected cardioversion electrode configuration, so that a unidirectional wavefront passes through said electrode configuration.

14. An implantable atrial cardioverting device according to claim 12, wherein the electrode of said atrial endocardial electrode lead is positively charged, the electrode of said ventricular endocardial electrode lead is negatively charged and the electrode of said subcutaneous electrode lead is uncharged when said discharge means discharges said stored electrical energy across said selected cardioversion electrode configuration, so that a unidirectional wavefront passes through said electrode configuration.

15. An implantable atrial cardioverting device according to claim 12, wherein the electrode of said atrial endocardial electrode lead is negatively charged, the electrode of said subcutaneous electrode lead is positively charged and the electrode of said ventricular endocardial electrode lead is uncharged when said discharge means discharges said stored electrical energy across said selected cardioversion electrode configuration, so that a unidirectional wavefront passes through said electrode configuration.

16. An implantable atrial cardioverting device according to claim 12, wherein the electrode of said subcutaneous electrode lead is a braid electrode, and wherein the electrode of said atrial endocardial electrode lead is negatively charged, the braid electrode of said subcutaneous electrode lead is positively charged and the electrode of said ventricular endocardial electrode lead is uncharged when said discharge means discharges said stored electrical energy across said selected cardioversion electrode configuration, so that a unidirectional wavefront passes through said electrode configuration.

17. An implantable atrial cardioverting device according to claim 12, wherein the electrode of said ventricular endocardial electrode lead is negatively charged, the electrode of said subcutaneous electrode lead is positively charged and the electrode of said atrial endocardial electrode lead is uncharged when said discharge means discharges said stored electrical energy across said selected cardioversion electrode configuration, so that a unidirectional wavefront passes through said electrode configuration.

18. An implantable atrial cardioverting device according to claim 12, wherein the electrode of said subcutaneous electrode lead is a braid electrode, and wherein the electrode of said ventricular endocardial electrode lead is negatively charged, the braid electrode of said subcutaneous electrode lead is positively charged and the electrode of said atrial endocardial electrode lead is uncharged when said discharge means discharges said stored electrical energy across said selected cardioversion electrode configuration, so that a unidirectional wavefront passes through said electrode configuration.

19. An implantable atrial cardioverting device according to claim 12, wherein the electrodes of said atrial endocardial electrode lead and said subcutaneous electrode lead are positively charged and the electrode of said ventricular endocardial electrode lead is negatively charged when said discharge means discharges said stored electrical energy across said selected cardioversion electrode configuration, so that a bidirectional wavefront passes through said electrode configuration.

20. An implantable atrial cardioverting device according to claim 12, wherein each of said electrodes is a braid electrode, and wherein the braid electrodes of said atrial endocardial electrode lead and said subcutaneous electrode lead are positively charged and the electrode of said ventricular endocardial electrode lead is negatively charged when said discharge means discharges said stored electrical energy across said selected cardioversion electrode configuration, so that a bidirectional wavefront passes through said electrode configuration.

21. An implantable atrial cardioverting device according to claim 12, wherein the electrodes of said atrial and ventricular endocardial electrode leads are braid electrodes and the electrode of said subcutaneous electrode lead is a patch electrode, and wherein the braid electrodes of said atrial endocardial electrode lead and said ventricular endocardial electrode lead are negatively charged and the patch electrode of said subcutaneous electrode lead is positively charged when said discharge means discharges said stored electrical energy across said selected cardioversion electrode configuration, so that a bidirectional wavefront passes through said electrode configuration.

22. An implantable atrial cardioverting device according to claim 12, wherein the electrodes of said atrial and ventricular endocardial electrode leads and the electrode of said subcutaneous lead are braid electrodes, and wherein the braid electrode of said ventricular endocardial electrode lead is negatively charged, the braid electrode of said subcutaneous electrode lead is positively charged and the braid electrode of said atrial endocardial electrode lead is uncharged when said discharge means discharges said stored electrical energy across said selected cardioversion electrode configuration, so that a unidirectional wavefront passes through said electrode configuration.

23. An implantable atrial cardioverting device according to claim 12, wherein the electrodes of said atrial and ventricular endocardial electrode leads and the electrode of said subcutaneous electrode lead are braid electrodes, and wherein the braid electrode of said atrial endocardial electrode lead is negatively charged, the braid electrode of said subcutaneous electrode lead is positively charged and the braid electrode of said ventricular endocardial lead is uncharged when said discharge means discharges said stored electrical energy across said selected cardioversion electrode configuration, so that a unidirectional wavefront passes through said electrode configuration.

24. An implantable atrial cardioverting device according to claim 12, wherein the electrodes of said atrial and ventricular endocardial electrode leads are braid electrodes and the electrode of said subcutaneous electrode lead is a patch electrode, and wherein the braid electrode of said atrial endocardial electrode lead is negatively charged, the patch electrode of said subcutaneous electrode lead is positively charged and the electrode of said ventricular endocardial electrode lead is uncharged when said discharge means discharges said stored electrical energy across said selected cardioversion electrode configuration, so that a bidirectional wavefront passes through said electrode configuration.

25. An implantable atrial cardioverting device according to any one of claims 1-24, further including means for delivering atrial and ventricular bradycardia and antitachycardia pacing therapy.

26. An implantable atrial cardioverting device according to any one of claims 3, 4, 8, 9, 10, 11 and 13-24, wherein the waveform of said discharged stored electrical energy is monophasic.

27. An implantable atrial cardioverting device according to any one of claims 3, 4, 8, 9, 10, 11 and 13-24 wherein the waveform of said discharged stored electrical energy is biphasic.

28. An implantable cardioverting/defibrillating device for the reversion of tachycardias, comprising:
means for storing electrical energy;
means for detecting the presence of an atrial tachycardia;
means for detecting the presence of a ventricular tachycardia;
an electrode lead system including a plurality of electrode leads therein, each of said leads including a cardioverting electrode having a substantially larger surface area and lower electrode impedance than the surface area and impedance of a pacing lead electrode, at least a first one of said leads being an atrial endocardial electrode lead and a second one of said leads being a ventricular endocardial electrode lead;
a plurality of atrial cardioversion electrode configurations, each of said configurations including at least two of said electrode leads;
a plurality of ventricular defibrillating electrode configurations, each of said configurations including at least two of said electrode leads;
first switching means responsive to the detection of an atrial tachycardia by said atrial tachycardia detecting means for selectively connecting said energy storage means to one of said atrial cardioversion electrode configurations;
second switching means responsive to the detection of a ventricular tachycardia by said ventricular tachycardia detecting means for selectively connecting said energy storage means to one of said ventricular defibrillating electrode configurations;
means for setting the level of electrical energy stored in said electrical energy storing means to an appropriate level for an atrial cardioversion shock;
means for setting the level of electrical energy stored in said electrical energy storing means to an appropriate level for a ventricular defibrillation shock; and,
means for discharging said stored electrical energy across a selected one of said atrial and ventricular electrode configurations.

29. An implantable cardioverting/defibrillating device according to claim 28, further including
means for sensing R-waves and delivering ventricular pacing pulses;
means responsive both to the detection of an atrial tachycardia and to the absence of an R-wave during a predetermined period of time following such detection for delivering a ventricular pacing pulse to produce a temporary ventricular refractory condition; and,
means for timing the delivery of said atrial cardioversion shock to occur during said temporary ventricular refractory condition.

30. An implantable atrial cardioverting device according to claim 29, further including
means responsive both to the detection of an trial tachycardia and to the detection of an R-wave during a predetermined period of time following such detection for timing the discharging of said stored electrical energy to synchronously occur during a ventricular refractory period which occurs following the R-wave.

31. An implantable cardioverting/defibrillating device according to claim 30, wherein said electrode lead system includes at least three electrode leads therein, wherein at least one of said electrode leads in said electrode lead system is a subcutaneous electrode lead, wherein at least one of said atrial cardioversion electrode configurations includes the electrode of said subcutaneous electrode lead and the electrode of said atrial endocardial electrode lead, and wherein at least one of said ventricular defibrillation electrode configurations includes the electrode of said subcutaneous electrode lead and the electrode of said ventricular endocardial electrode lead.

32. An implantable cardioverting/defibrillating device according to any one of claims 28-30, wherein the electrode of said atrial endocardial lead is negatively charged and the electrode of said ventricular endocardial electrode lead is positively charged when said discharging means discharges said stored electrical energy across said selected one of said atrial and ventricular electrode configurations, so that a unidirectional wavefront passes through said electrode configuration.

33. An implantable cardioverting/defibrillating device according to any one of claims 28-30, wherein the electrode of said atrial endocardial electrode lead is positively charged and the electrode of said ventricular endocardial electrode lead is negatively charged when said discharging means discharges said stored electrical energy across said selected one of said atrial and ventricular electrode configurations, so that a unidirectional wavefront passes through said electrode configuration.

34. An implantable cardioverting/defibrillating device according to claim 31, wherein the electrode of said atrial endocardial electrode lead is negatively charged, the electrode of said ventricular endocardial electrode lead is positively charged and the electrode of said subcutaneous electrode lead is uncharged when said discharge means discharges said stored electrical energy across said selected one of said atrial and ventricular electrode configurations, so that a unidirectional wavefront passes through said electrode configuration.

35. An implantable cardioverting/defibrillating device according to claim 31, wherein the electrode of said atrial endocardial electrode lead is positively charged, the electrode of said ventricular endocardial electrode lead is negatively charged and the electrode of said subcutaneous electrode lead is uncharged when said discharge means discharges said stored electrical energy across said selected one of said atrial and ventricular electrode configurations, so that a unidirectional wavefront passes through said electrode configuration.

36. An implantable cardioverting/defibrillating device according to claim 31, wherein the electrode of said atrial endocardial electrode lead is negatively charged, the electrode of said subcutaneous electrode lead is positively charged and the electrode of said ventricular endocardial electrode lead is uncharged when said discharge means discharges said stored electrical energy across said selected one of said atrial and ventricular electrode configurations, so that a unidirectional wavefront passes through said electrode configuration.

37. An implantable cardioverting/defibrillating device according to claim 31, wherein the electrodes of said atrial and ventricular endocardial electrode leads are negatively charged and the electrode of said subcutaneous electrode lead is positively charged when said discharge means discharges said stored electrical energy across said selected one of said atrial and ventricular electrode configurations, so that a bidirectional wavefront passes through said electrode configuration.

38. An implantable cardioverting/defibrillating device according to claim 31, wherein the electrode of said ventricular endocardial electrode lead is negatively charged, the electrode of said subcutaneous electrode lead is positively charged and the electrode of said atrial endocardial electrode lead is uncharged when said discharge means discharges said stored electrical energy across said selected one of said atrial and ventricular electrode configurations, so that a unidirectional wavefront passes through said electrode configuration.

39. An implantable cardioverting/defibrillating device according to claim 31, wherein the electrodes of said atrial endocardial electrode lead and said subcutaneous electrode lead are positively charged and the electrode of said ventricular endocardial electrode lead is negatively charged when said discharge means discharges said stored electrical energy across said selected one of said atrial and ventricular electrode configurations, so that a bidirectional wavefront passes through said electrode configuration.

40. An implantable cardioverting/defibrillating device according to any one of claims 31 and 34-39, wherein each of said electrodes is a braid electrode.

41. An implantable cardioverting/defibrillating device according to any one of claims 31 and 34-39, wherein the electrodes of said atrial and ventricular endocardial electrode leads are braid electrodes and wherein the electrode of said subcutaneous electrode lead is patch electrode.

42. An implantable cardioverting/defibrillating device according to any one of claims 28-31, wherein the waveform of said discharged stored electrical energy is monophasic.

43. An implantable cardioverting/defibrillating device according to any one of claims 28-31, wherein the waveform of said discharged stored electrical energy is biphasic.

44. An implantable cardioverting/defibrillating device according to any one of claims 28-31, further including means for delivering atrial and ventricular bradycardia and antitachycardia pacing therapy.

45. A method of operating an implantable atrial tachycardia cardioverting device, said device including an electrode lead system having a plurality of electrode leads therein, each of which leads includes a cardioverting electrode having a substantially larger surface area and lower electrode impedance than the surface area and electrode impedance of a pacing lead electrode, at least one of said leads being an atrial endocardial electrode lead, said device further including a plurality of atrial cardioversion electrode configurations, each of said configurations including at least two of said electrode leads, said method comprising the steps of:

A) detecting the presence of an atrial tachycardia;
B) storing a charge of electrical energy at an appropriate level for an atrial cardioversion shock;
C) connecting said stored charge of electrical energy to one of said electrode configurations;
D) delivering cardioversion shock therapy across said one of said electrode configurations;
E) determining whether said shock therapy has reverted said atrial tachycardia and, if it has not,
F) storing another charge of electrical energy at an appropriate level for an atrial cardioversion shock;
G) connecting said stored other charge of electrical energy to another one of said electrode configurations; and,
H) delivering cardioversion shock therapy across said other one of said electrode configurations.

46. A method of operating an implantable atrial tachycardia cardioverting device according to claim 45, wherein one of said electrode leads comprises a subcutaneous electrode lead, and wherein said step C) of connecting said stored charge of electrical energy to one of said electrode configurations comprises the sub-step of connecting said stored charge of electrical energy to an electrode configuration that includes said atrial endocardial electrode lead and said subcutaneous electrode lead.

47. A method of operating an implantable atrial tachycardia cardioverting device according to claim 46, wherein said sub-step includes the further substep of connecting said stored charge of electrical energy to said electrode configuration in such a manner that the electrode of said atrial endocardial electrode lead receives a negative charge and the electrode of said subcutaneous electrode lead receives a positive charge when said cardioversion shock therapy is delivered, whereby a unidirectional cardioversion wavefront passes through said electrode configuration upon such delivery.

48. A method of operating an implantable atrial tachycardia cardioverting device according to claim 45, wherein said electrode lead system includes three electrode leads therein, one of said electrode leads being a subcutaneous electrode lead and another of said electrode leads being a ventricular endocardial electrode lead, said method including the further step of:
I) Repeating steps E), F), G), and H).

49. A method of operating an implantable atrial tachycardia cardioverting device according to claim 45, wherein one of said electrode leads comprises a ventricular endocardial electrode lead, and wherein said step C) of connecting said stored charge of electrical energy to one of said electrode configurations comprises the sub-step of connecting said stored charge of electrical energy to an electrode configuration that includes said atrial endocardial electrode lead and said ventricular endocardial electrode lead.

50. A method of operating an implantable atrial tachycardia cardioverting device according to claim 49, wherein said sub-step includes the further substep of connecting said stored charge of electrical energy to said electrode configuration in such a manner that the electrode of said atrial endocardial electrode lead receives a negative charge and the electrode of said ventricular endocardial electrode lead receives a positive charge when said cardioversion shock therapy is delivered, whereby a unidirectional cardioversion wavefront passes through said electrode configuration upon such delivery.

51. A method of operating an implantable atrial tachycardia cardioverting device according to claim 45, wherein said electrode lead system includes three electrode leads therein, one of said electrode leads being a subcutaneous electrode lead and another of said electrode leads being a ventricular endocardial electrode lead, and wherein said step C) of connecting said stored charge of electrical energy to one of said electrode configurations comprises the sub-step of connecting said stored charge of electrical energy to said electrode configuration in such a manner that the electrode of said atrial endocardial electrode lead receives a negative charge, the electrode of said ventricular endocardial electrode lead receives a positive charge and the electrode of said subcutaneous electrode lead receives no charge when said cardioversion shock therapy is delivered, whereby a unidirectional cardioversion wavefront passes through said electrode configuration upon such delivery.

52. A method of operating an implantable atrial tachycardia cardioverting device according to claim 45, wherein said electrode lead system includes three electrode leads therein, one of said electrode leads being a subcutaneous electrode lead and another of said electrode leads being a ventricular endocardial electrode lead, and wherein said step C) of connecting said stored charge of electrical energy to one of said electrode configurations comprises the sub-step of connecting said stored charge of electrical energy to said electrode configuration in such a manner that the electrode of said atrial endocardial electrode lead receives a negative charge, the electrode of said subcutaneous electrode lead receives a positive charge and the electrode of said ventricular endocardial electrode lead receives no charge when said cardioversion shock therapy is delivered, whereby a unidirectional cardioversion wavefront passes through said electrode configuration upon such delivery.

53. A method of operating an implantable atrial tachycardia cardioverting device according to claim 45, wherein said electrode lead system includes three electrode leads therein, one of said electrode leads being a subcutaneous electrode lead and another of said electrode leads being a ventricular endocardial electrode lead, and wherein said step C) of connecting said stored charge of electrical energy to one of said electrode configurations comprises the sub-step of connecting said stored charge of electrical energy to said electrode configuration in such a manner that the electrodes of said atrial endocardial electrode lead and said subcutaneous patch electrode lead each receive a positive charge, and the electrode of said ventricular endocardial electrode lead receives a negative charge when said cardioversion shock therapy is delivered, whereby a bidirectional cardioversion wavefront passes through said electrode configuration upon such delivery.

54. A method of operating an implantable atrial tachycardia cardioverting device according to claim 45, wherein said electrode lead system includes three electrode leads therein, one of said electrode leads being a subcutaneous electrode lead and another of said electrode leads being a ventricular endocardial electrode lead, and wherein said step C) of connecting said stored charge of electrical energy to one of said electrode configurations comprises the sub-step of connecting said stored charge of electrical energy to said electrode configuration in such a manner that the electrode of said atrial endocardial electrode lead receives no charge, the electrode of said ventricular endocardial electrode lead receives a negative charge and the electrode of said subcutaneous electrode lead receives a positive charge when said cardioversion shock therapy is delivered, whereby a unidirectional cardioversion wavefront passes through said electrode configuration upon such delivery.

55. A method of operating an implantable atrial tachycardia cardioverting device according to claim 45, wherein said electrode lead system includes three electrode leads therein, one of said electrode leads being a subcutaneous electrode lead and another of said electrode leads being a ventricular endocardial electrode lead, and wherein said step C) of connecting said stored charge of electrical energy to one of said electrode configurations comprises the sub-step of connecting said stored charge of electrical energy to said electrical configuration in such a manner that the electrode of said atrial endocardial electrode lead receives a positive charge, the electrode of said ventricular endocardial electrode lead receives a negative charge and the electrode of said subcutaneous electrode lead receives no charge when said cardioversion shock therapy is delivered, whereby a unidirectional cardioversion wavefront passes through said electrode configuration upon such delivery.

56. A method of operating an implantable atrial tachycardia cardioverting device according to claim 45, which, prior to the step (D) delivery of cardioversion shock therapy, includes the sub-steps of awaiting the occurence of an R-wave during a predetermined time period following the detection of said atrial tachycardia; in the absence of the occurence of an R-wave during said predetermined time period, delivering a ventricular pacing pulse to produce a temporary ventricular refractory condition; and, timing the delivery of the step (D) cardioversion shock therapy to occur during said temporary ventricular refractory condition.

57. A method of operating an implantable atrial tachycardia cardioverting device according to claim 45, which, prior to the step (D) delivery of cardioversion shock therapy, includes the sub-steps of awaiting the occurence of an R-wave during a predetermined time period following the detection of said atrial tachycardia; and, if an R-wave is detected during said time period, timing the delivery of the step (D) cardioversion shock therapy to synchronously occur during a ventricular refractory period which occurs following said R-wave.

58. A method of operating an implantable tachycardia converting device, said device including an electrode lead system having a plurality of electrode leads therein, each of which leads includes a cardioverting electrode having a substantially larger surface area and lower impedance than the surface area and impedance of a pacing lead electrode, at least one of said leads being an atrial endocardial electrode lead and one of said leads being a ventricular endocardial electrode lead, said device further including a plurality of cardioversion electrode configurations, each of said configurations including at least two of said electrode leads, said method comprising the steps of:
   A) detecting the presence of a tachycardia and classifying the tachycardia as either an atrial or a ventricular tachycardia;
   B) storing a charge of electrical energy at an appropriate level for delivering cardioversion shock therapy corresponding to the type of tachycardia detected;
   C) connecting said stored charge of electrical energy to one of said electrode configurations;
   D) delivering said corresponding cardioversion shock therapy across said one of said electrode configurations;
   E) again detecting the presence of a tachycardia and classifying the tachycardia as either an atrial or a ventricular tachycardia;
   F) storing another charge of electrical energy at an appropriate level for delivering cardioversion shock therapy corresponding to the type of the tachycardia detected in step (E);
   G) connecting said stored other charge of electrical energy to another one of said electrode configurations; and,
   H) delivering said corresponding cardioversion shock therapy across said other one of said electrode configurations.

59. A method of operating an implantable tachycardia cardioverting device according to claim 58, wherein said electrode lead system includes three electrode leads therein, one of said electrode leads being a subcutaneous electrode lead, said method including the further steps of:
   I) repeating steps E), F), G) and H).

* * * * *